(12) United States Patent
Radisic et al.

(10) Patent No.: US 9,096,643 B2
(45) Date of Patent: Aug. 4, 2015

(54) CELL-PROTECTIVE PEPTIDES AND USES THEREOF

(76) Inventors: Milica Radisic, Toronto (CA); Susan Dallabrida, Lynn, MA (US); Maria Ann Rupnick, Medford, MA (US)

( * ) Notice: Subject to any disclaimer, the term of this patent is extended or adjusted under 35 U.S.C. 154(b) by 0 days.

(21) Appl. No.: 13/819,055

(22) PCT Filed: Aug. 26, 2011

(86) PCT No.: PCT/CA2011/000969
§ 371 (c)(1),
(2), (4) Date: Jul. 24, 2013

(87) PCT Pub. No.: WO2012/024784
PCT Pub. Date: Mar. 1, 2012

(65) Prior Publication Data
US 2013/0303457 A1    Nov. 14, 2013

Related U.S. Application Data

(60) Provisional application No. 61/377,666, filed on Aug. 27, 2010.

(51) Int. Cl.
| | | |
|---|---|---|
| A61K 35/12 | (2006.01) | |
| C07K 7/06 | (2006.01) | |
| A61K 9/00 | (2006.01) | |
| A61K 47/48 | (2006.01) | |
| C07K 5/11 | (2006.01) | |
| C07K 14/515 | (2006.01) | |
| C12N 5/00 | (2006.01) | |
| C12N 5/077 | (2010.01) | |
| A61K 38/00 | (2006.01) | |

(52) U.S. Cl.
CPC ............... *C07K 7/06* (2013.01); *A61K 9/0024* (2013.01); *A61K 47/4823* (2013.01); *A61K 47/48784* (2013.01); *C07K 5/1019* (2013.01); *C07K 14/515* (2013.01); *C12N 5/0068* (2013.01); *C12N 5/0657* (2013.01); *A61K 35/12* (2013.01); *A61K 38/00* (2013.01); *C12N 2533/50* (2013.01); *C12N 2533/72* (2013.01)

(58) Field of Classification Search
None
See application file for complete search history.

(56) References Cited

FOREIGN PATENT DOCUMENTS

WO    WO 2009/008990    *    1/2009

OTHER PUBLICATIONS

Rask et al., J. Biomed. Mater Res. A, 2010, 95, pp-105-117.*
Dallabrida et al., Circulation Research, 2005, 96, e8-e24.*

* cited by examiner

Primary Examiner — Karlheinz R Skowronek
Assistant Examiner — Roy Teller
(74) Attorney, Agent, or Firm — Wolf, Greenfield & Sacks, P.C.

(57) ABSTRACT

A peptide comprising the amino acid sequence, $X_1X_2RX_3DX_4X_5X_6X_7$ is provided, as well as a biomaterial comprising the peptide for use to treat conditions resulting from cell death or apoptosis.

10 Claims, 24 Drawing Sheets

SEQUENCE LISTING

```
<160> NUMBER OF SEQ ID NOS: 21

<210> SEQ ID NO 1
<211> LENGTH: 16
<212> TYPE: PRT
<213> ORGANISM: Artificial Sequence
<220> FEATURE:
<223> OTHER INFORMATION: Peptide hydrogel

<400> SEQUENCE: 1

Arg Ala Arg Ala Asp Ala Asp Ala Arg Ala Arg Ala Asp Ala Asp Ala
1               5                   10                  15
```

```
<210> SEQ ID NO 2
<211> LENGTH: 7
<212> TYPE: PRT
<213> ORGANISM: Artificial Sequence
<220> FEATURE:
<223> OTHER INFORMATION: angiopoietin 1 peptide

<400> SEQUENCE: 2

Gln His Arg Glu Asp Gly Ser
1               5

<210> SEQ ID NO 3
<211> LENGTH: 9
<212> TYPE: PRT
<213> ORGANISM: Artificial Sequence
<220> FEATURE:
<223> OTHER INFORMATION: cell-protective peptide
<220> FEATURE:
<221> NAME/KEY: MISC_FEATURE
<222> LOCATION: (1)..(1)
<223> OTHER INFORMATION: X may be glutamine, threonine, serine or
      asparagine
<220> FEATURE:
<221> NAME/KEY: MISC_FEATURE
<222> LOCATION: (2)..(2)
<223> OTHER INFORMATION: X is a positively charged amino acid
<220> FEATURE:
<221> NAME/KEY: MISC_FEATURE
<222> LOCATION: (4)..(4)
<223> OTHER INFORMATION: X is glutamic acid, threonine, isoleucine,
      histidine, lysine, glutamine, tyrosine, valine or leucine
<220> FEATURE:
<221> NAME/KEY: MISC_FEATURE
<222> LOCATION: (6)..(6)
<223> OTHER INFORMATION: X is glycine or valine
<220> FEATURE:
<221> NAME/KEY: MISC_FEATURE
<222> LOCATION: (7)..(7)
<223> OTHER INFORMATION: X may be serine, threonine, aspartic acid,
      isoleucine or glycine
<220> FEATURE:
<221> NAME/KEY: MISC_FEATURE
<222> LOCATION: (8)..(8)
<223> OTHER INFORMATION: X may be leucine, valine, glutamine, glycine,
      isoleucine or serine
<220> FEATURE:
<221> NAME/KEY: MISC_FEATURE
<222> LOCATION: (9)..(9)
<223> OTHER INFORMATION: X may be aspartic acid, asparagine, valine or
      lysine

<400> SEQUENCE: 3

Xaa Xaa Arg Xaa Asp Xaa Xaa Xaa Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: cell protective peptide

<400> SEQUENCE: 4

Arg Glu Asp Gly
1

<210> SEQ ID NO 5
<211> LENGTH: 4
<212> TYPE: PRT
<213> ORGANISM: Artificial Sequence
<220> FEATURE:
```

```
<223> OTHER INFORMATION: cell protective peptide

<400> SEQUENCE: 5

Arg Leu Asp Gly
1

<210> SEQ ID NO 6
<211> LENGTH: 5
<212> TYPE: PRT
<213> ORGANISM: Artificial Sequence
<220> FEATURE:
<223> OTHER INFORMATION: cell protective peptide

<400> SEQUENCE: 6

Arg Glu Asp Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: cell protective peptide

<400> SEQUENCE: 7

Arg Leu Asp Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: cell protective peptide

<400> SEQUENCE: 8

His Arg Glu Asp Gly
1               5

<210> SEQ ID NO 9
<211> LENGTH: 5
<212> TYPE: PRT
<213> ORGANISM: Artificial Sequence
<220> FEATURE:
<223> OTHER INFORMATION: cell protective peptide

<400> SEQUENCE: 9

His Arg Leu Asp Gly
1               5

<210> SEQ ID NO 10
<211> LENGTH: 6
<212> TYPE: PRT
<213> ORGANISM: Artificial Sequence
<220> FEATURE:
<223> OTHER INFORMATION: cell protective peptide

<400> SEQUENCE: 10

His Arg Glu Asp Gly Ser
1               5

<210> SEQ ID NO 11
<211> LENGTH: 6
<212> TYPE: PRT
<213> ORGANISM: Artificial Sequence
<220> FEATURE:
<223> OTHER INFORMATION: cell protective peptide
```

<400> SEQUENCE: 11

His Arg Leu Asp Gly Ser
1               5

<210> SEQ ID NO 12
<211> LENGTH: 6
<212> TYPE: PRT
<213> ORGANISM: Artificial Sequence
<220> FEATURE:
<223> OTHER INFORMATION: cell protective peptide

<400> SEQUENCE: 12

Gln His Arg Glu Asp Gly
1               5

<210> SEQ ID NO 13
<211> LENGTH: 6
<212> TYPE: PRT
<213> ORGANISM: Artificial Sequence
<220> FEATURE:
<223> OTHER INFORMATION: cell protective peptide

<400> SEQUENCE: 13

Gln His Arg Leu Asp Gly
1               5

<210> SEQ ID NO 14
<211> LENGTH: 7
<212> TYPE: PRT
<213> ORGANISM: Artificial Sequence
<220> FEATURE:
<223> OTHER INFORMATION: cell protective peptide

<400> SEQUENCE: 14

Gln His Arg Glu Asp Val Ser
1               5

<210> SEQ ID NO 15
<211> LENGTH: 7
<212> TYPE: PRT
<213> ORGANISM: Artificial Sequence
<220> FEATURE:
<223> OTHER INFORMATION: cell protective peptide

<400> SEQUENCE: 15

Gln His Arg Leu Asp Gly Ser
1               5

<210> SEQ ID NO 16
<211> LENGTH: 6
<212> TYPE: PRT
<213> ORGANISM: Artificial Sequence
<220> FEATURE:
<223> OTHER INFORMATION: cell protective peptide

<400> SEQUENCE: 16

Lys Arg Leu Asp Gly Ser
1               5

<210> SEQ ID NO 17
<211> LENGTH: 8
<212> TYPE: PRT
<213> ORGANISM: Artificial Sequence
<220> FEATURE:
<223> OTHER INFORMATION: cell protective peptide

```
<400> SEQUENCE: 17

Gln His Arg Glu Asp Gly Ser Leu
1               5

<210> SEQ ID NO 18
<211> LENGTH: 8
<212> TYPE: PRT
<213> ORGANISM: Artificial Sequence
<220> FEATURE:
<223> OTHER INFORMATION: cell protective peptide

<400> SEQUENCE: 18

Gln His Arg Leu Asp Gly Ser Leu
1               5

<210> SEQ ID NO 19
<211> LENGTH: 9
<212> TYPE: PRT
<213> ORGANISM: Artificial Sequence
<220> FEATURE:
<223> OTHER INFORMATION: cell protective peptide

<400> SEQUENCE: 19

Gln His Arg Leu Asp Gly Ser Leu Asp
1               5

<210> SEQ ID NO 20
<211> LENGTH: 9
<212> TYPE: PRT
<213> ORGANISM: Artificial Sequence
<220> FEATURE:
<223> OTHER INFORMATION: cell protective peptide

<400> SEQUENCE: 20

Gln His Arg Glu Asp Gly Ser Leu Asp
1               5

<210> SEQ ID NO 21
<211> LENGTH: 7
<212> TYPE: PRT
<213> ORGANISM: Artificial Sequence
<220> FEATURE:
<223> OTHER INFORMATION: scrambled peptide

<400> SEQUENCE: 21

Asp Gly Gln Glu Ser His Arg
1               5
```

CELL-PROTECTIVE PEPTIDES AND USES THEREOF

RELATED APPLICATIONS

This application is a national stage filing under 35 U.S.C. 371 of International Application PCT/CA2011/000969, filed Aug. 26, 2011, which claims priority to U.S. Provisional Application No. 61/377,666, filed on Aug. 27, 2010, the content of which is hereby incorporated by reference herein.

FIELD OF THE INVENTION

The present invention generally relates to peptides having cell-protective properties.

BACKGROUND OF THE INVENTION

Myocardial infarction (MI) results in cardiomyocyte death in the infarct zone followed by scar formation and pathological remodelling of the ventricle. Myocardium does not regenerate and viable tissue remaining is often insufficient to maintain adequate cardiac output. Heart transplants are often not an available or appropriate option. Thus, there is a pressing need for alternative interventions, such as cell replacement therapy.

The first evidence that cell replacement therapy may be a viable intervention for the treatment of MI came from animal studies showing that injection of fetal or neonatal cardiomyocytes (CM) improved left ventricular function and ventricle thickness in the post-MI setting. Injected CM integrated with host CM through gap junctions and intercalated discs. Yet one of the main limitations of these studies and a most probable reason for the incomplete functional recovery was the massive death of injected myocytes.

In most myocardial cell injection studies, the cells were suspended in a liquid such as saline or culture medium followed by intramyocardial or coronary injection. The main challenges associated with this procedure were poor survival of the injected cells and washout from the injection site. According to some estimates, 90% of cells delivered through a needle leaked out of the injection site. In addition, a significant number of cells (~90%) died within days after injection.

Thus, developing improved delivery and localization methods (e.g. hydrogels) and effective anti-cell death strategies could significantly improve effectiveness of cell injection procedures. Towards that goal, Kofidis et al. (Balsam, Wagers et al. 2004; Kofidis, Lebl et al. 2005), reported that injection of Matrigel or Matrigel plus embryonic stem cells (ESC) into infarcted rat hearts resulted in structural stabilization, prevented wall thinning and improved fractional shortening. Chirstman et al. (Christman, Fok et al. 2004; Christman, Vardanian et al. 2004) demonstrated that injection of skeletal myoblasts into myocardial infarcts using fibrin matrix increased cell localization within the infarct after five weeks, reduced infarct size and increased vascularization without causing a marked inflammatory response or foreign body reaction. Similarly, Ryu Hee et al (Ryu, Kim et al. 2005) found that injection of bone marrow mononuclear cells into cryoinjured rat myocardium using fibrin matrix increased the amount of viable tissue, improved microvessel formation and reduced the amount of fibrous tissue in comparison to the injection of cells in culture medium or culture medium alone. (Laflamme, Gold et al. 2005) Laflamme and Murry demonstrated that using Matrigel modified with a number of biomolecules to target multiple pathways related to cell survival, significantly increased the grafting of the human ESC-derived CM injected into infracted rat hearts (Laflamme, Chen et al. 2007).

It was also demonstrated that a synthetic material, self-assembling peptide hydrogel, could be utilized for cell injection into the myocardium (Davis, Motion et al. 2005). Upon injection, the peptide formed a nano-fibrous structure that promoted recruitment of endogenous cells expressing endothelial markers, and supported survival of injected CM. The peptide consisted of alternating hydrophilic and hydrophobic domains (AcN-RARADADARARADADA-CNH) (SEQ ID NO: 1) and did not activate integrin signalling. Insulin-like growth factor-1 bound to the self-assembling peptide improved grafting and survival of CM injected into infarcted myocardium (Davis, Hsieh et al. 2006). Photocrosslinkable PEGylated fibrinogen was recently demonstrated to be an excellent substrate for encapsulation and cultivation of CM derived from neonatal rat hearts and human ESC-derived CM. The cells cultivated in these hydrogels were connected to each other via gap junctions and demonstrated significant cross-striations (Shapira-Schweitzer, Habib et al. 2009).

Recent studies collectively indicate that an injection of hydrogel alone, without the reparative cells, may also attenuate pathological remodeling upon myocardial infarction (Landa, Miller et al. 2008; Dobner, Bezuidenhout et al. 2009; Fujimoto, Ma et al. 2009; Leor, Tuvia et al. 2009). It is thought that hydrogels act by changing the ventricular geometry and mechanics, thus reducing elevated local wall stresses that have been implicated in pathological remodeling (Wall, Walker et al. 2006). Finite element modeling of wall stresses indicated that upon injection of the material of elastic modulus 10–20 kPa in the infarct, injection improved ejection fraction and the stroke volume/end-diastolic volume relationship. In addition, injections of the material in the border zone decreased end-systolic fiber stress proportionally to the volume and the stiffness of the injected material.

Angiopoietin 1 (ang1) is known to preserve cardiac function post-MI (Siddiqui, Blomberg et al. 2003) (Zhou, Ma et al. 2005) in animal models. Ang1 interacts directly with CM via integrins to promote adhesion, survival, cardioprotective signalling (akt/MAPK) and prevent induced apoptosis (Dallabrida, Ismail et al. 2005). CMs survived better on immobilized ang1 then on most other matrices present in the heart. Ang1 lacks known integrin-binding motifs, but the novel site QHREDGS (SEQ ID NO: 2) was identified (Dallabrida, Ismail et al. 2005). Further, ang1/integrin interactions attenuated cardiac hypertrophy in vivo (Dallabrida, Ismail et al. 2008).

Low survival rate during culture and passaging of human induced pluripotent stem (iPS) cells presents a major obstacle in research; especially hindering further manipulations during induction and differentiation processes to obtain functional cells for regenerative therapies. Recent reports suggest that the addition of Y-27632, a selective inhibitor of p160-Rho-associated coiled-coil kinase (ROCK), to culture media permits survival of dissociated human ES cells during passaging without compromising pluripotency or differentiation potential. However, because Rho/ROCK can activate different signaling cascades depending on cell type and environmental context, as well as contribute to changes in the cytoskeleton, it is possible that treatment of human iPS cells with its inhibitor, Y-27632, may result in less than favorable conditions for the subsequent differentiation of these cells.

It would be desirable, thus, to develop survival promoting means effective to treat conditions involving cell death and apoptosis.

SUMMARY OF THE INVENTION

A novel cell-protective peptide derived from angiopoietin 1 has now been identified which is useful to prevent, or at least reduce, cell death and apoptosis.

Thus, in one aspect of the invention, a non-naturally occurring peptide is provided comprising the amino acid sequence, $$X_1X_2RX_3DX_4X_5X_6X_7 \quad \text{(SEQ ID NO:3)},$$

wherein:

$X_1$ is an optional residue that may be glutamine, threonine, serine or asparagine;

$X_2$ is an optional residue that may be a positively charged amino acid such as histidine, arginine or lysine;

$X_3$ is glutamic acid, threonine, isoleucine, histidine, lysine, glutamine, tyrosine, valine or leucine;

$X_4$ may be glycine or valine;

$X_5$ is optional residue that may be serine, threonine, aspartic acid, isoleucine or glycine;

$X_6$ is an optional residue that may be leucine, valine, glutamine, glycine, isoleucine or serine; and $X_7$ is an optional residue that may be aspartic acid, asparagine, valine or lysine.

In another aspect of the invention, a biomaterial conjugate is provided comprising a peptide as defined above.

In another aspect of the invention, a method of treating a pathological condition resulting from reduced angiopoietin 1 activity is provided comprising administration of a non-naturally occurring peptide comprising the amino acid sequence, $X_1X_2RX_3DX_4X_5X_6X_7$, as defined above.

In a further aspect of the invention, a method of treating a cardiac condition in a mammal is provided comprising the step of administering to a mammal a non-naturally occurring peptide comprising the amino acid sequence, $X_1X_2RX_3DX_4X_5X_6X_7$, as defined above.

In a further aspect of the invention, a method of promoting stem cell survival is provided comprising incubating stem cells with a non-naturally occurring peptide comprising the amino acid sequence, $X_1X_2RX_3DX_4X_5X_6X_7$, or a biomaterial conjugate comprising the peptide.

These and other aspects of the invention are described in the detailed description that follows by reference to the figures.

DETAILED DESCRIPTION OF THE INVENTION

Figure 1:
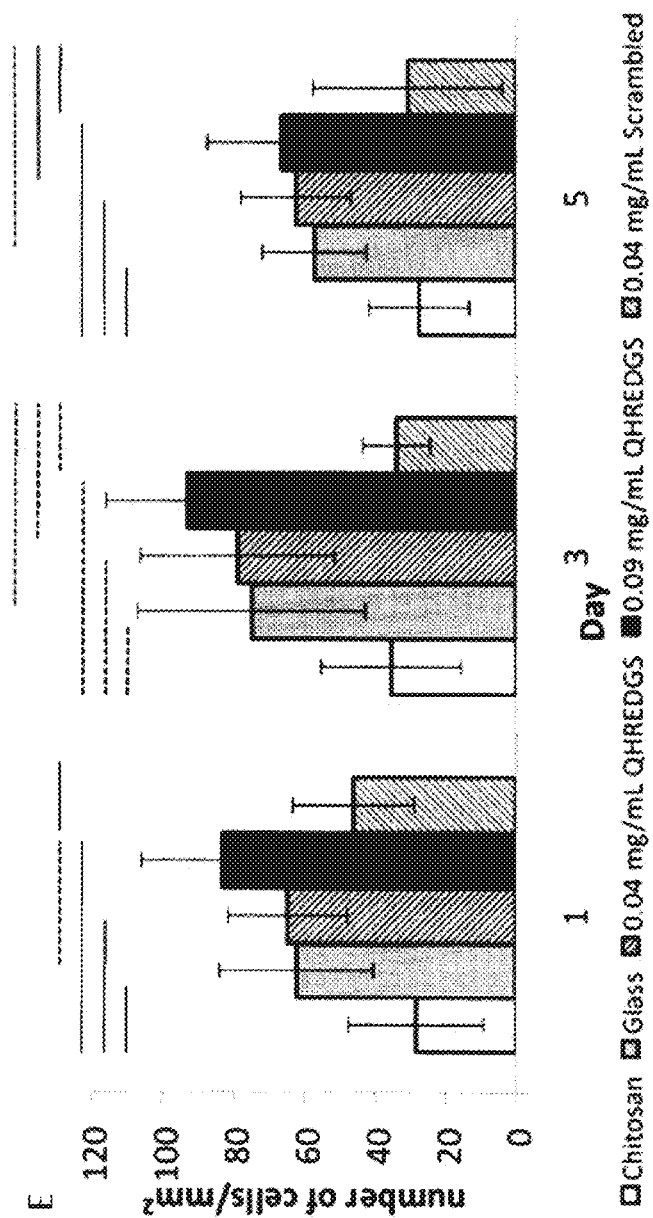
FIG. 1 graphically illustrates the number of cells adhering to QHREDGS-modified surfaces in comparison to control surfaces.

A cell-protective peptide is provided, as well as a biomaterial conjugate comprising the cell-protective peptide.

The term "cell-protective" is used herein to encompass peptides that prevent or at least reduce an adverse effect on a cell, e.g. cell death or apoptosis. In this regard, the cell-protective peptide has been determined to exhibit integrin-binding activity, and cell-protective properties similar to angiopoietin 1 such as prevention of cell death and apoptosis on exposure taxol, doxorubicin, peroxide treatment, hypoxia, ischemia, serum starvation and/or low glucose.

The present cell-protective peptide is useful to treat conditions involving cell death, including necrosis and autophagy, and apoptosis, which may or may not result from, or result in, lack of angiopoietin 1 activity. Such conditions include cardiac and vascular disease or injury including congestive heart failure, ischemic diseases such as myocardial infarction, peripheral vascular disease, ischemic renal disease, cerebral vascular disease, reperfusion injury from cardiac catheterization, thrombolytic therapy, cardiac bypass surgery and peripheral vascular bypasses, side effects of cardiotoxic drugs (i.e. oncologic agents) and radiation, injury during procedures with reduced/suspended circulation, e.g. preservation of donor organs for transplant (cell protective peptide may be included in perfusate), following resuscitation circulatory bypass (include peptide in infusate during cooling procedures), during cell replacement therapy (protection of cardiac and other organs) including myocytes, stem cells and mixed cell populations, and hypertension such as systemic hypertension and subsequent organ damage, or pulmonary hypertension, promotion of local cardiac function/healing from use of devices such as stents, patches and closure devices), preservation of cardiac function in setting of other diseases, e.g. metabolic syndrome/diabetes and provide enhanced function in heart failure by improving energetics and metabolism; pulmonary disease such as asthma, pulmonary edema, pulmonary hypertension, adult respiratory distress syndrome and acute lung injury; kidney disease including renal protection from toxic injury, drugs (e.g. cyclosporine), sepsis, hemorrhagic shock and chronic hypoxia/fibrosis insults, ischemia reperfusion injury and renal protection from endotoxemia; neurologic diseases or injury such as stroke, spinal cord injury and peripheral nerve injury; ocular diseases including diabetic retinopathy; bone marrow disease (by supporting hematopoesis and regulation of stem cell production); gastrointestional conditions including ulcers and ascites; protection from oxidative injury; treatment of diseases characterized by edema/hyperpermeability such as pulmonary edema, sepsis, anaphalaxis, adult respiratory distress syndrome, lymphangioedema, anasarca, CNS swelling, ascites, hemorrhagic shock, thyroid disease and some drug overdoses; and protection of injury resulting from radiation therapy.

The non-naturally occurring cell protective peptide in accordance with the invention comprises the ang1 peptide sequence,

wherein:

$X_1$ is an optional residue that may be glutamine, threonine, serine or asparagine;

$X_2$ is an optional residue that may be a positively charged amino acid such as histidine, arginine or lysine;

$X_3$ is glutamic acid, threonine, isoleucine, histidine, lysine, glutamine, tyrosine, valine or leucine;

$X_4$ may be glycine or valine;

$X_5$ is optional residue that may be serine, threonine, aspartic acid, isoleucine or glycine;

$X_6$ is an optional residue that may be leucine, valine, glutamine, glycine, isoleucine or serine; and $X_7$ is an optional residue that may be aspartic acid, asparagine, valine or lysine.

The peptide may be linear, cyclic, cross-linked or immobilized as long as the cell-protective activity of the peptide is retained. In addition, the peptide may form a broad U-shape to assume the native structural characteristics of this peptide as it exists in angiopoietin 1.

The peptide may include modifications which do not substantially affect the U-shape of the core residues so as to retain the cell-protective activity of the peptide, e.g. integrin-binding activity. For example, the peptide may be modified to include one or more additional amino acid residues at either the C- or N-termini, or to include a terminal protecting group that may function to stabilize the peptide, protect the peptide from undesirable degradation or improve the activity thereof. Any chemical group which serves to protect peptide ends may be used. Useful N-terminal protecting groups include, for example, lower alkanoyl groups of the formula R—C(O)— wherein R is a linear or branched lower alkyl chain comprising from 1-5 carbon atoms. Examples of N-terminal protecting groups include the acetyl group and amino acid analogues lacking the amino function. Examples of suitable carboxyl terminal protecting groups include, for example, ester-forming alkyl groups, particularly lower alkyl groups such as methyl, ethyl and propyl, as well as amide-forming amino functions such as primary amine (—NH2), as well as monoalkylamino and dialkylamino groups such as methylamino, ethylamino, dimethylamino, diethylamino, methylethylamino and the like. C-terminal protection can also be achieved using a decarboxylated amino acid analogue, such as agmatine. Of course, N- and C-protecting groups of even greater structural complexity may alternatively be incorporated, if desired.

The peptide may also be modified at one or more of its core amino acid residues, for example, to include a derivatized R-group. Suitable modifications include those which may stabilize the U-shape of the peptide, to optimize the activity thereof, or which function to protect the peptide from degradation.

In particular embodiments of the invention, the peptide may be selected from the following group of peptides: REDG (SEQ ID NO: 4), RLDG (SEQ ID NO: 5), REDGS (SEQ ID NO: 6), RLDGS (SEQ ID NO: 7), HREDG (SEQ ID NO: 8), HRLDG (SEQ ID NO: 9), HREDGS (SEQ ID NO: 10), HRLDGS (SEQ ID NO: 11), QHREDG (SEQ ID NO: 12), QHRLDG (SEQ ID NO: 13), QHREDVS (SEQ ID NO: 14), QHREDGS (SEQ ID NO: 2), QHRLDGS (SEQ ID NO: 15), KRLDGS (SEQ ID NO: 16), QHREDGSL (SEQ ID NO: 17), QHRLDGSL (SEQ ID NO: 18), QHRLDGSLD (SEQ ID NO: 19) and QHREDGSLD (SEQ ID NO: 20).

The present peptide can readily be prepared using standard, well-established solid-phase peptide synthesis methods (SPPS), either manually or using peptide synthesis instruments, as one of skill in the art will appreciate. In addition, modifications such as those described above, may also be readily accomplished using well-established chemistry. Once a selected cell-protective peptide is prepared, it may be purified using standard purification techniques to the required degree to meet standards for therapeutic use.

The cell-protective peptide may be administered to cells alone or in combination with at least one pharmaceutically acceptable adjuvant. The expression "pharmaceutically acceptable" means acceptable for use in the pharmaceutical and veterinary arts, i.e. not being unacceptably toxic or otherwise unsuitable. Examples of pharmaceutically acceptable adjuvants include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered traganeanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods.

In another aspect, the cell-protective peptide may be physically or covalently immobilized onto a biomaterial to form a cell-protective biomaterial useful for administration to a target site in a mammal to be treated, e.g. to the heart. Suitable biomaterials for this purpose will generally be i) biocompatible, ii) biodegradable, and iii) mechanically stable enough to withstand the environment into which they are administered, e.g. the beating environment of the heart. Suitable biomaterials may be pre-formed films, or 3 dimensional porous or fibrous scaffolds. The biomaterials may also be injectable, so that they can be applied with a syringe in a minimally invasive manner. Examples of suitable biomaterials include, but are not limited to, natural biomaterials such as polysaccharides, e.g. chitosan, alginate, agarose, methylcellulose, hyaluronan, collagen (e.g. collagen I, collagen II and collagen IV), laminin, matrigel, fibronectin, vitronectin, poly-1-lysine, proteoglycans, fibrin glue, gels made by decellularization of engineered and natural tissues as well as embryoid bodies. Also included as suitable biomaterials are synthetic biomaterials such as polyglycolic acid (PGA), polylactic acid (PLA) and combinations of PGA and PLA such as PLGA, poly ε-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self assembling peptide hydrogels such as AcN-RARADADARARADADA-CNH (but not limited to this sequence), polyurethanes, poly(isopropylacrylamide), and poly(N-isopropylacrylamide)[poly(NIPAM)]. Combinations of any of these materials may also be used as well as chemically modified forms thereof such as carboxylated or aminated forms.

Immobilization of the cell-protective peptide onto the biomaterial is achieved using physical and chemical immobilization methodologies well-established in the art. For example, the selected peptide may be immobilized onto the biomaterial using carbodiimide (e.g. EDC) or click chemistry. Other immobilization mechanisms and chemistries are possible, e.g. using photo-initiated chemistries, avidin-biotin interactions, thiol bonds, and the like. Preferably, the biomaterial is modified to accommodate immobilization of the peptide thereon. For example, the biomaterial may be modified to include a linker such as azidobenzoic acid to which the peptide may be linked for immobilization on the biomaterial. The biomaterial will generally incorporate an amount of cell-protective peptide that is effective for cell protection. For example, the biomaterial may incorporate an amount of about 0.05-5 micromoles of cell-protective peptide per gram of biomaterial.

The cell-protective peptide may be administered to cells to prevent, or reduce, cell death. The peptide may be administered in any suitable form, including in a composition or biomaterial as described above in an amount suitable to confer protection on the cells. The peptide may be administered to a mammal to treat cells in vivo, or may be administered to cells ex vivo, or in culture.

In one embodiment, the cell-protective peptide or biomaterial conjugate is suitable for administration to cardiac cells for cardiac cell protection. The term "cardiac cell" is used herein to encompass the different cell types present in the heart including fibroblasts, endothelial cells, smooth muscle cells and cardiomyocytes. The cell-protective peptide may be applied as a systemic drug for treatment of heart disease, such as congestive heart failure, or ischemic diseases such as myocardial infarction. Alternatively, a cell-protective biomaterial may be injected, e.g. intramyocardially during a CABG procedure or transendocardially via an intraventricular catheter.

The cell-protective peptide may also be used ex vivo to preserve cardiac cells, e.g. in a donor heart for transplant, in cardiospheres derived from biopsies in cultures of cardiac cells, etc. In this aspect, the cell-protective peptide may be included in the perfusate in a soluble form or a controlled release form.

It has also been determined that the cell-protective peptide is useful to protect stem cells, in vivo as well as ex vivo. The term "stem cells" includes, but is not limited to, adipose stem cells, mesenchymal stem cells, induced pluripotent stem cells, hematopoietic stem cells, and progenitors derived from stem cells such as cardiovascular progenitors (that may be identified by markers such as Flk1, KDR, PDGFRalpha, NRx2.5, Sca-1, c-kit, isl1, GATA4, Tbx18). In this aspect, the cell-protective peptide has been determined to prevent apoptosis, enhance viability and increase colony number, while having little or no adverse effect on pluripotency and proliferation rate of the stem cells.

Appropriate dosages of the cell-protective peptide can readily be determined by one of skill in the art. In one embodiment, dosages of up to about 500 micromolar are contemplated for administration to cells for protection against cell death and apoptosis.

Embodiments of the invention are described in the following specific examples, which are not to be construed as limiting.

Example 1

In Vitro Protection of Cardiomyocytes

Synthesis of Az-Chitosan

Az-chitosan was synthesized according to a procedure previously described (Yeo, Geng et al. 2007), the relevant contents of which are incorporated herein by reference, with modification. Chitosan (75% to 90% deacyetelated chitin, Novamatrix, Norway) 400 mg was dissolved in 15 mL of distilled water. A mass of 140 mg of 1-ethyl-3-(-3-dimethylaminopropyl)carbodiimide HCl (EDC, Thermo Scientific) was dissolved in 1 mL of distilled water and 80 mg of 4-azidobenzoic acid (ABA, TCI America) was dissolved in 1 mL of DMSO (Sigma). A 300 µL aliquot of N,N,N',N'-Tetramethylethylenediamine (TEMED, Sigma) was added to the ABA solution followed by the EDC solution. This final solution was added drop-wise to the dissolved chitosan solution. The pH of the solution was adjusted to 6 using 1N hydrochloric acid (HCl, VWR) and the pH meter (pH 720, inoLab). After 10 min the pH of the solution was adjusted to 5 using 1N HCl. The reaction solution was left to react in the dark overnight.

The product was centrifuged at $11.5 \times 10^3$ g for 2 hours in the microcentrifuge. The precipitate of unreacted azidobenzoic acid was removed, and the supernatant, which contained the Az-chitosan, was collected into a 50 mL conical tube. The pH of the solution was increased to 9.5 using 1 N sodium hydroxide (NaOH, VWR) to precipitate the Az-chitosan. The tube was centrifuged at $15.2 \times 10^3$ g for 10 min, the supernatant that contained the impurities such as unreacted ABA and reactants was aspirated. The Az-chitosan pellet was dispersed in 80 mL of distilled water. These solutions underwent the first purification, which involved adjusting the pH to 3 with 1N HCl to dissolve the Az-chitosan, and then increasing pH to 9.5 to precipitate out the pure Az-chitosan. The tubes were centrifuged at $15.2 \times 10^3$ g for 10 min, the supernatant was aspirated off and the pellet was dispersed in 80 mL of distilled water. This purification step was repeated until the absorbance of the supernatant was less than 0.01 at 270 nm on the spectrometer. This absorbance corresponds to ABA and thus a low absorbance indicated that most of the unreacted ABA has been removed. After the final wash the pellet was resuspended in 40 mL of distilled water and the pH was adjusted to 5 using 1 N HCl. This solution was then lyophilized for 3 days and stored at $-20°$ C. until use.

Conjugation of Peptides to Az-Chitosan

Conjugation of peptides to Az-chitosan was performed using EDC chemistry. Az-chitosan was dissolved at 10 mg/mL in distilled water and filtered through a 0.2 µm. The peptides were dissolved at 10 mg/ml in PBS. These reagents were combined with EDC and S—NHS in distilled water to yield the volume of 500 µl of the final reaction solution consisting of 5 mg/ml of Az-chitosan, 4.8 mg/mL of EDC (Thermo Scientific), 13.2 mg/mL of S—NHS (Thermo Scientific) and the peptide QHREDGS at 1 and 3 mg/mL. The reaction proceeded for 3 hr at room temperature in dark.

The surfaces for the caspase assay involved a similar reaction. Az-chitosan was dissolved at 20 mg/mL in 0.9% saline and the peptides (QHREDGS and scrambled peptide DGQE-SHR) were dissolved at 20 mg/mL in PBS, and RGDS (purchased from American Peptide) was dissolved at 10 mg/mL in PBS. The reagents were combined with the powder form of EDC and S—NHS to get a final reaction solution of 13.5 mg/mL of Az-chitosan, 1.8 mg/mL EDC, 4.95 mg/mL S—NHS and 6.1 mg/mL of QHREDGS or scrambled peptide; or 3.4 mg/mL of RGDS. The molar concentrations of RGDS and QHREDGS in the reaction solution and per mass of chitosan were similar (QHREDGS: 7.3 mM in reaction solution or 0.55 µmol/mg chitosan; RGDS: 7.8 mM in reaction solution or 0.57 µmol/mg chitosan). The reaction proceeded for 3 hr at room temperature in dark. Thus, the final reaction solution listed above, was diluted 6.6 times in PBS and reacted for 6 hr at room temperature. This solution was dialyzed in a Spectra/Por dialysis membrane (Spectra/Por MWCO 3500, Spectum Labs) for 1.5 days and lyophilized for 2 days.

Characterization of Peptide Modified Chitosan

1H-NMR

Samples were prepared by adding the dry chitosan to a mixture of one mL of 98% $D_2O$ and 2% D-acetic acid and analyzed by $^1$H-NMR spectroscopy by Bruker DRX500 at the Purdue Interdepartmental NMR Facility (Number of scans: 32).

Concentration of Covalently Bound QHREDGS in Az-Chitosan

The covalent binding of QHREDGS to Az-chitosan was confirmed and quantified using a fluorescently labeled form of this peptide, with FITC conjugated to the N terminus of the QHREDGS peptide. A stock solution of 20 mg/mL was created by dissolving FITC-QHREDGS in PBS. This stock was then serially diluted to create 11 standards ranging from 0.05 µg/mL to 50 µg/mL. The standards were read by a fluorometer (Molecular Devices) at an excitation wavelength of 490 nm and an emission of 520 nm. The samples of Az-chitosan-QHREDGS were prepared as described above using 1 mg/mL and 3 mg/mL FITC-QHREDGS in the reaction solution. A total of two samples were prepared for each reaction. The samples were then dialyzed (Spectra/Por MWCO 3500, Spectrum Labs) against distilled water for 1 hour to remove unreacted peptide and the fluorescence of the peptide modified product was determined using a fluorometer as described for the standard curve. All of the samples were run at a pH of 7 as the fluorescence is greatly affected by changes in pH.

The concentration of fluorescent peptide present in the reaction solution post dialysis was determined by comparing the level of fluorescence against standards. The volume in the dialysis membrane increased to 620 µL after dialyzation and this volume was used to determine the mass of the conjugated peptide presented in Table 1. The molecular weight cut off of the dialysis membrane was at most a tenth the size of chitosan, so it was assumed that the membrane retained all of the chitosan. Therefore the mass of Az-chitosan was the amount initially used in the reaction (2.5 mg). The moles of peptide present on the cell culture surfaces was estimated by calculating the moles of peptide in 90 µl of solution post-dialysis, since this is the volume used to prepare cell culture surfaces.

Isolation of Neonatal Rat CMs

Neonatal (1 to 2 day-old) Sprague-Dawley rats were euthanized according to the procedure approved by the University of Toronto Committee on Animal Care. The hearts were removed, quartered and the cells were isolated by an overnight treatment with trypsin (4° C., 6120 units/mL in 1-lank's Balanced Salt Solution, HBSS) followed by serial collagenase digestion (220 units/ml in HBSS) as described in (Radisic, Park et al. 2004), the relevant contents of which are incorporated herein by reference. The supernatant from 5 collagenase digests of the tissues was collected and centrifuged at 750 rpm (94 g) for 4 min, resuspended in culture medium and pre-plated into T75 flasks (Falcon) for 1 hour to separate the non-adherent cells (enriched CMs) from the adherent cells (non-myocytes). The enriched CMs were used in the studies. The CM culture medium consisted of Dulbecco's Modified Eagle Medium (DMEM) with 4.5 g/L glucose, 4 mM L-glutamine, 10% certified fetal bovine serum (FBS), 100 U/mL penicillin, 100 µg/mL streptomycin, and 10 mM 4-2-hydroxyethyl-1-piperazineethanesulfonic acid buffer (HEPES, Gibco/Invitrogen).

Coating of Glass Slides with Peptide Modified Chitosan and Cell Seeding

The surfaces used for microscopy analysis were created on circular 12 mm diameter glass coverslips (VWR). These were plasma treated (WS-400BZ-6NPP/Lite, Laurell Technologies) for 30 s. Each charged coverslip received 90 µL of the reacted material. The peptide modified chitosan (90 µl) was spin-coated at 4000 rpm for 5 seconds to create a thin uniform layer of the hydrogel on top of the glass coverslip. The UV lamp (UVP, 365 nm, 1 mW/cm$^2$ at 3" distance, 115 V, 60 Hz, 0.16 Amp) was placed above the coverslip at a distance of 5 mm for 5 min. The surface was then washed in a 70% ethanol for 1 minute, to sterilize the material, and placed in a well of a 12-well plate with 1 mL of Dulbecco's phosphate buffered saline (PBS, Gibco).

The day before cells were ready to be seeded, the surfaces in the 12-well plates were sterilized by germicidal UV illumination overnight. The PBS surrounding the surfaces was then aspirated off and 100,000 live cells were pipetted onto each surface in 100 µL of culture media. These surfaces were left in the incubator for 20 to 30 min to allow the cells to begin to adhere, and then supplemented with 1 mL of warm CM media. The cells were cultivated for 8 days, with 100% culture media change every 2-3 days. The initial seeding density of heart cells on peptide-chitosan coated surfaces was 88 cells/mm$^2$. Controls included a glass coverslip, which supports cell attachment, a glass coverslip coated with Az-chitosan alone, which does not support cell attachment, and a glass coverslip coated with Az-chitosan-DGQESHR (scrambled QHREDGS peptide). Each type of surface was created in triplicate.

Preliminary Cell Encapsulation Studies

The lyophilized form of the peptide-modified Az-chitosan was dissolved in sterile 0.9% saline at 12 mg/mL. CMs (2.5×10$^6$) were suspended in 15 µL of CM culture media with 30% serum for 15 minutes on ice. These cells were then suspended in 35 µL of the hydrogel and crosslinked in the transwell inserts of the 96 well plates. The cells were cultivated in the CM culture medium with 10% FBS for up to 4 days.

Scanning Electron Microscopy

The glass slides coated with thin layers of Az-chitosan and Az-chitosan-QHREDGS were analyzed by scanning electron microscopy (SEM) to visualize the surfaces at the Microscopy Imaging Laboratory, University of Toronto. This was carried out using an environmental chamber (S-3400 N, Hitachi) and a total of two samples were analyzed for each type of surface.

Brightfield Microscopy and Cell Counts

Brightfield images were taken with 10× magnification of surfaces with cells (N=3) to visualize the morphology and cell attachment (IX81, Olympus). In order to take representative images of a surface, five images were taken at different areas. The number of cells was then counted using the cell counting plug-in on ImageJ (NIH version 1.36b).

Live/Dead Staining

Live dead staining was performed using 5-carboxyfluorescein diacetate acetoxymethly ester (CFDA, Invitrogen), which stains live cells green, and with propidium iodide (PI, Invitrogen), which stains dead cells red, according to the manufacturer's instruction. The samples were incubated in 10 µM of CFDA and 75 µL/mL of PI in PBS for 45 min at 37° C. Three different surfaces were analyzed for each type of sample (N=3) and a total of five images were taken for each surface to get a full representation of the viability of the cells on a surface. In order to quantify the viability, the numbers of live and dead cells were counted separately using the cell counter plug-in on ImageJ.

Immunostaining for Cardiac Troponin I

The immunostaining against cardiac troponin I was performed on cells fixed with 4 w/v % paraformaldehyde (PFA, Sigma). The samples were submersed in a blocking solution composed of 10% normal horse serum (NHS, Vector Laboratories) in PBS for 40 min at room temperature. This solution was removed and the sample was submersed in a solution containing primary antibody for 1 hour at 37° C. This solution was made from 0.5% tween 20 (Sigma), 1.5% NHS, primary antibody of mouse anti-cardiac troponin I (Millipore) at a dilution of 1:100 in PBS. The samples were washed three times with PBS for 2 min, and the secondary antibody solution was added for 30 min at room temperature. This solution was made up of 0.5% Tween 20, 1.5% NHS, and a FITC-conjugated goat anti-mouse IgG (Sigma) at 1:100 and 2-(4-Amidinophenyl)-6-indolecarbamidine dihydrochloride (DAPI, Sigma) at 1:200 in PBS. Three 2 min PBS washes were conducted. The samples were mounted onto coverslides using mounting media, and could be stored at 4° C. until they were imaged. Each sample was made in triplicate and five pictures were taken of each surface to have an adequate representation for quantification. The numbers of nuclei were determined by counting the number of DAPI stained nuclei using the cell counting plugin on ImageJ. The number of CMs was determined by counting the number of successfully stained Troponin I cells.

Caspase Assay

Glass coverslips were coated with Az-chitosan, or Az-chitosan conjugated with QHREDGS, RGDS, or a scrambled peptide (DGQESHR). The cells were then seeded (100,000 cells in 50 µL of CM media; seeding density of 88 cells/mm$^2$) on each surface (N=3), including plain glass as a control, for 15 min. The cells were then supplemented with serum-free media. After 19 hours, 5 µL of taxol (paclitaxel, Sigma), dissolved at 100 µM in DMSO, was added and maintained for 17 hours and 45 min at which time caspase assay was performed. One set of glass surfaces was not exposed to taxol treatment as a negative control.

The Apo-ONE caspase assay (Promega) was performed according to manufacturer's protocol. The cells were permeabilized and lyzed to release the caspases, which are activated in cells undergoing apoptosis. The assay contains rhodamine 110, bis-(N-CBZ-L-aspartyl-L-glutamyl-L-valyl-L-aspartic acid amide; Z-DEVD-R110). Caspase 3 and 7 are known to cleave the peptide DEVD and the leaving group, rhodamine 110 becomes fluorescent when excited with fluorescent light. The amount of fluorescence is proportional to the level of caspase 3/7 activity in the sample. According to the manufacturer's protocol, the caspase substrate was dissolved in a buffer at 1:100. The buffer, 200 µl, was applied to the cells for 7 hours at room temperature. The lysis buffer was then removed from each well and placed into a black 96 well plate. The fluorescence of the buffer was read in the fluorometer at an excitation of 485 nm and a cut off of 520 nm. These values were in RFU and were divided by the number of cells remaining on each sample to give the RFU/sample. The number of attached cells was estimated based on the difference between the seeded cell number and the number of non-adherent cells removed from the wells prior to the addition of the lysis buffer. Since this was a short duration experiment (35 hr 45 min) in serum free media, cell proliferation was not significant as confirmed by visual observation.

Statistics

The data is represented as averages ± standard deviations. All statistical analyses were conducted using a one-way ANOVA with a post-hoc Tukey test or ANOVA on ranks with Sigma Stat version 3.0 (SYSTAT software). Statistical analysis was performed only on data sets that had a minimum of three independent samples (N=3). The differences were considered statistically significant when $p<0.05$. All data sets were tested for normality and equality of variance.

Results

QHREDGS peptide was conjugated to photocrosslinkable chitosan (Az-chitosan), a biodegradable and biocompatible material. The material was coated on a glass slide as a thin layer, and the ability of QHREDGS peptide conjugated to Az-chitosan to promote the attachment and survival of CMs was evaluated. Scanning electron micrographs of Az-chitosan and Az-chitosan-QHREDGS confirmed that the material was present on the glass slide.

$^1$H-NMR was performed on Az-chitosan and confirmed successful azidobenzoic acid modification of chitosan (Chitosan: 1.99 ppm (s), 3.0 (m, broad), 3.2-4 (m); 4-azidobenzoic acid: 7.17-7.19 ppm (d, J=10 Hz), 7.81-7.83 (d, J=10 Hz)). Conjugation of 4-azidobenzoic acid to chitosan was calculated by comparing an integrated area of peaks in 7-8 ppm (4H, benzene) and that in 3-4 ppm (6H, chitosan). Approximately 1% of amino groups in chitosan were conjugated with 4-azidobenzoic acid. The ¹H-NMR was not sensitive enough to detect the peptide in the presence of abundant chitosan backbone.

Conjugation of QHREDGS to Az-chitosan was quantified using a fluorescently tagged peptide. The final concentrations of the peptide bound to Az-chitosan are displayed in Table 1 for two different amounts of peptide used in the reaction. The amounts were less than what would be obtained for 100% conjugation efficiency, but confirmed that the peptide was present after the washing steps.

TABLE 1

Quantification of covalent binding of QHREDGS to Az-chitosan from fluorescently tagged peptide

| Concentration of QHREDGS in reaction solution (mg/ml) | Concentration of fluorescently tagged QHREDGS in Az-chitosan post dialysis (mg/mL) | Mass QHREDGS/ Mass of Az-chitosan (mg/mg) | Moles of peptide in hydrogel on surface (nmol) |
|---|---|---|---|
| 1 | 0.04 | $10 \times 10^{-3}$ | 3.8 |
| 3 | 0.09 | $22 \times 10^{-3}$ | 8.3 |

Brightfield images of the cells were taken after 1, 3 and 5 days of cell incubation on the surfaces. There was more cell attachment to the surfaces coated with Az-chitosan-QHREDGS compared to the surfaces coated with Az-chitosan-DGQESHR. The glass and Az-chitosan-QHREDGS modified surfaces showed similar cell attachment levels, while Az-chitosan showed little cell attachment, a result which was quantified via cell counting as shown in FIG. 1. Spontaneous contractions appeared after 2-3 days of cultivation for the peptide modified chitosans as well as the glass controls, but not on Az-chitosan alone. Quantification showed that the surface coated with QHREDGS conjugated to Az-chitosan had significantly greater cell adhesion in comparison with surfaces coated with peptide-free Az-chitosan or the scrambled-peptide conjugated Az-chitosan. These findings indicated that the peptide sequence QHREDGS promoted heart cell adhesion to the chitosan hydrogel. In addition, the attachment response was specific to the peptide as a whole, and not just the individual amino acids, as the scrambled peptide did not have the same attachment results. It was also noted that the higher concentration of QHREDGS peptide did not increase the cell attachment significantly, indicating a saturated response. The fact that we did not observe significant cell attachment on samples coated with Az-chitosan evidences that the glass slides are indeed well coated with the hydrogel.

Figure 2:
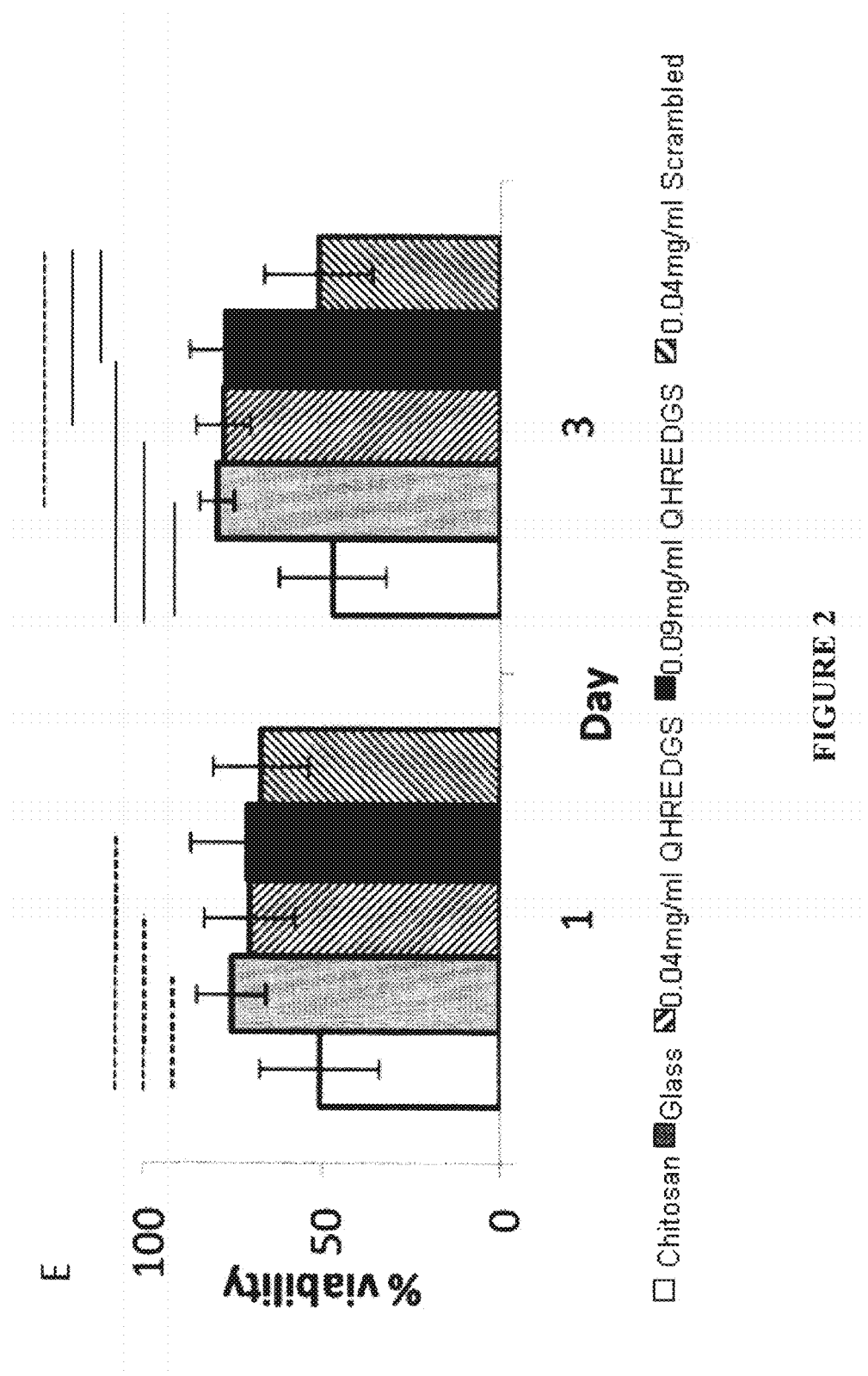
FIG. 2 graphically illustrates heart cell viability on QHREDGS-modified surfaces in comparison to control surfaces.

The hydrogel surfaces were then subjected to live/dead staining to determine whether the material maintained the viability of the cells. The surfaces were stained after one and three days of incubation since most of the cell death occurs within the first three days of cultivation. Images showed a higher cell viability for the glass and Az-chitosan-QHREDGS surfaces in comparison to the other controls, and also confirmed that there was more cell attachment to QHREDGS peptide modified surfaces. These observations were quantified with image analysis (FIG. 2). It was found that the surfaces coated with QHREDGS peptide conjugated to Az-chitosan had a significantly greater cell viability than surfaces coated with the peptide-free Az-chitosan after one and three days of incubation as well as the scrambled peptide conjugated to Az-chitosan (Az-chitosan-DGQESHR) after three days of incubation. Therefore, the peptide sequence QHREDGS was not only enhancing the total number of cells attached to the surface containing this peptide, but also increased the viability of the cells attaching to the surfaces. Since heart cell viability was comparable between the 0.04 and 0.09 mg/ml concentrations of QHREDGS in the hydrogel, the lower concentration was used for further studies.

In addition, the preliminary studies provided evidence of heart cell elongation when encapsulated in three-dimensional (3D) Az-chitosan-QHREDGS hydrogels and cultivated for 4 days. In the control hydrogels, Az-chitosan alone and the scrambled peptide modified chitosan (Az-chitosan-DGQESHR), a large number of dead round cells are noted in the hydrogels after 1 day of 3D culture. These preliminary data illustrate the importance of the QHREDGS peptide for the heart cell survival and elongation when encapsulated in these covalently crosslinked hydrogels in 3D.

Figure 3:
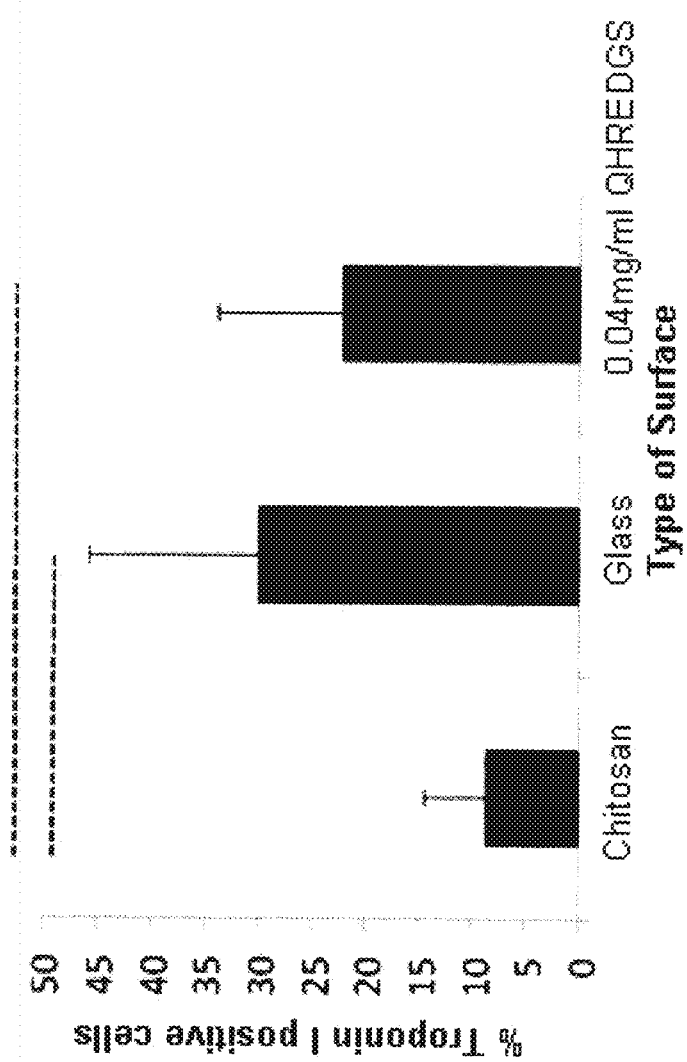
FIG. 3 graphically illustrates the percentage of cardiomyocyte cells identified by Troponin T staining on different surfaces after 8 days of culture.

Primary cells isolated from the neonatal rat hearts are a heterogeneous mixture of many cell types including fibroblasts, endothelial cells, smooth muscle cells as well as CM. The isolate used in this work contains a cell population enriched with CM, but does not exclude the other cardiac cell types. Staining for cardiac troponin I was performed after 8 days of cultivation to ensure that the cell population that remained adherent to the QHREDGS modified Az-chitosan surfaces contained CMs and not just the other cell types present in the heterogeneous heart cell population. This incubation time was chosen as neonatal CMs should mature, assemble a contractile apparatus and stain for cardiac troponin I after this time period. There were CM present on day 8 in all conditions and an increase in the percentage of troponin I positive cells on Az-chitosan-QHREDGS compared to Az-chitosan alone (FIG. 3).

Figure 4:
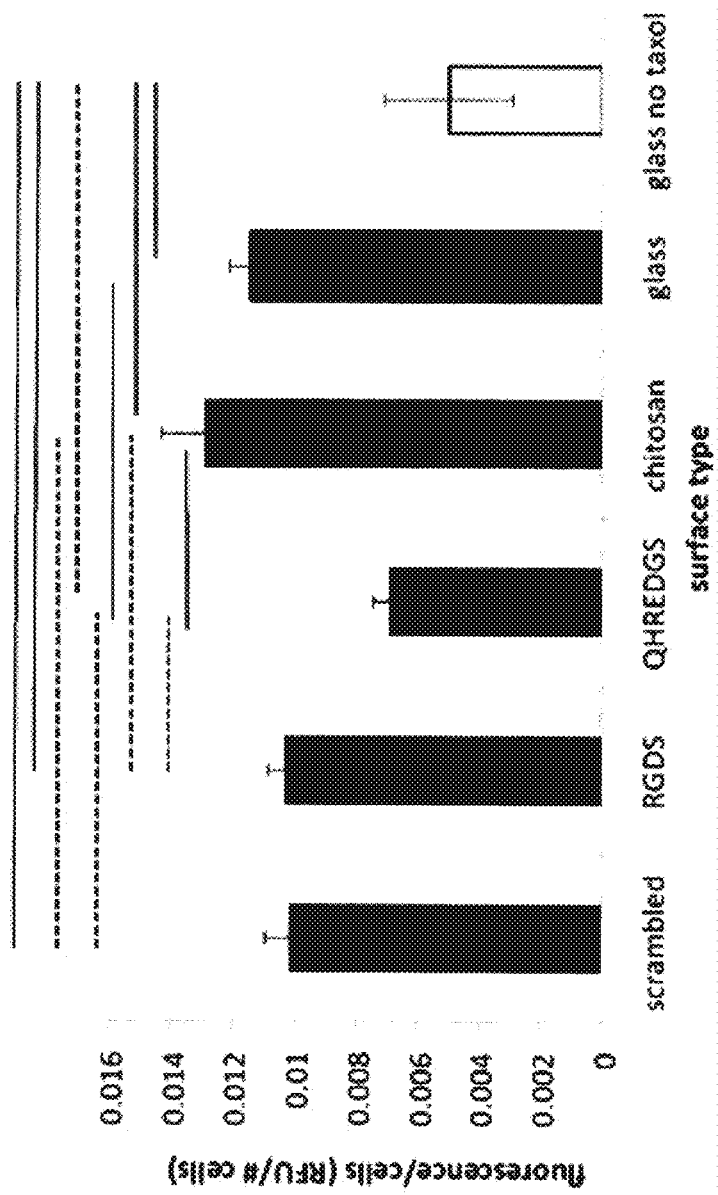
FIG. 4 graphically illustrates the level of apoptosis in cells adhered to QHREDGS-modified surfaces in comparison to control surfaces after an overnight taxol treatment.

The effect of the Az-chitosan-QHREDGS on heart cell apoptosis was determined using a caspase 3/7 assay. The heart cells were serum-starved and incubated with taxol to induce apoptosis as previously described (Dallabrida, Ismail et al. 2005; Saji, Fukumoto et al. 2007), the relevant contents of which are incorporated herein by reference. The family of cysteine proteins, caspases, is central to apoptotic pathways. Caspase 3 is an important mediator of end stage apoptosis that is activated post-MI and contributes to progressive cardiac injury. Cells cultured on QHREDGS modified Az-chitosan had significantly lower levels of caspase-3/7 activation compared to all control groups which included: RGDS modified Az-chitosan, scrambled peptide modified Az-chitosan, peptide-free Az-chitosan or glass (FIG. 4). In contrast, a commonly used RGD peptide did not exhibit the anti-apoptotic effect on heart cells, although the peptide can promote attachment of CM. The results demonstrate that the levels of caspase 3/7 activation in cells cultivated on Az-chitosan-RGDS was similar to those in the cells cultivated on Az-chitosan-DGQESHR (scrambled QHREDGS), indicating that typical RGD-based engagement of integrins was insufficient to prevent apoptosis.

Example 2

In Vivo Protection of Cardiomyocytes

Isolation of Neonatal Rat Cardiomyocytes

All animal experimental procedures were approved by the Animal Care Committee of the Toronto General Research Institute and the University of Toronto Committee on Animal Care, according to the Guide for the Care and Use of Laboratory Animals. Neonatal (1 to 2 day-old) Sprague-Dawley (in vitro studies) or Lewis rats (in vivo studies) were euthanized, hearts were removed and primary cardiomyocytes isolated as described in Example 1. The cardiomyocyte culture medium consisted of Dulbecco's Modified Eagle medium with 4.5 g/L glucose, 4 mM L-glutamine, 10% FBS and 100 U/mL penicillin/streptomycin. Cells were maintained in a humidified 5% $CO_2$ incubator at 37° C.

Monolayer Studies

Hydrogen Peroxide Treatment

Rat neonatal cardiomyocytes were incubated for 1.5 hr with 500 μM QHREDGS, scrambled (scram) QHREDGS peptide (DGQESHR), or PBS control (PBS); 200 nM ang 1 or its matched buffer control [0.1% bovine serum albumin (BSA) in PBS] in the culture medium. The culture medium consisted of Dulbecco's Modified Eagle's Medium (DMEM) with 0.5% BSA and cytosine-β-D-arabinofuranoside (antiproliferative). Reactive oxygen species were increased by addition of 100 μM $H_2O_2$ for 10 min (37° C., 5% $CO_2$) (N=6/group). Cell viability was measured using a Trypan blue stain. Trypan blue dye is impermeable to viable cells, but enters dead/damaged cells with impaired membrane integrity, staining cells blue.

Doxorubicin Induced Apoptosis and Caspase Activation

Rat neonatal cardiomyocytes were given doxorubicin (Dox) to induce apoptosis and PBS or peptide QHREDGS (1 d), Western blotting was conducted and levels assessed via densitometric analysis (Scion Image software). Graphs show levels of inactive versus active caspase-3. Levels of inactive caspase-6 were normalized to GAPDH.

Adenosine Triphosphate (ATP) Assay

Rat neonatal cardiomyocytes were incubated with PBS (control), 500 μM QHREDGS, scrambled QHREDGS peptide, GRGDSP peptide or 400 nM ang 1 or ang2 in DMEM/ 0.5% BSA/cytosine-β-D-arabinofuranoside (37° C., 5% $CO_2$, 1 d). ATP levels were quantified using the CellTiter-Glo Luminescent Assay (Promega) as per manufacturer's instructions (N=6/group). Luminescence was measured using a Wallac 1420 microplate reader.

Properties

Mechanical Testing

Az-chitosan was dissolved at 10 mg/mL and 20 mg/mL in 0.9% saline, and 100 pit of the material was placed on 12 mm circular glass coverslides and crosslinked for 5 minutes as described above. The samples were stored submersed in PBS in 12 well plates. To determine the stiffness of the gels, micropipette aspiration (MA) was used. Pipettes with an internal diameter of 0.21 mm were used to apply pressure locally in the centre of the gels. The pipette diameter was less than the thickness of the gel, ensuring that only the stiffness of the gels and not the underlying glass was measured. Pipette placement was controlled by a micromanipulator. Pressure was applied using a 20 mL air filled syringe attached to a linear actuator, which applied 0.01-0.05 cm steps (~1-3 kPa) at 400 Hz controlled by LabView. The maximum applied pressure was 6-14 kPa. Images were captured immediately after each step using PSRemote through a Navitar 12× zoom lens connected to a digital camera. Three to four measurements were made per gel concentration. Aspiration lengths for each step were measured and normalized to the pipette diameter. The initial elastic modulus (representative of the physiological range) was estimated using an analytical halfspace model that is commonly applied to analyze MA data.

Degradation Studies

A volume of 100 μl of 10 mg/mL Az-chitosan, QHREDGS modified Az-chitosan, and RGDS modified A-chitosan, were placed on the coverslip and crosslinked with UV light for 5 min as described above. The coverslip with the material was placed in the Petri dish and the mass of this entire system determined. Cardiomyocyte culture media containing 10% fetal bovine serum (FBS), was added to the Petri dish and the samples were stored in the 37° C. incubator to simulate the conditions used for cell culture and in vivo studies. To assess the weight of the material at different time points, the media was aspirated and the mass of the sample in the petri dish measured.

Cardiomyocyte Encapsulation System

The lyophilized form of the peptide-modified Az-chitosan (Az-chitosan-QHREDGS or Az-chitosan-RGDS) was dissolved in sterile 0.9% PBS at 12 mg/mL. Cardiomyocytes ($2.5 \times 10^6$) were suspended in 15 μL 30% FBS-containing culture medium for 15 min. on ice. These cells were further suspended in 35 μL of the hydrogel. This mixture was placed on a 12 mm diameter glass coverslip, which was placed on a UV lamp (UVP, 365 nm, 1 mW/$cm^2$ at 3" distance, 115 V, 60 Hz, 0.16 Amp) and exposed to UV light for 5 min. The samples were then transferred to a 12 well plate and supplemented with 2 mL of warm cardiomyocyte culture media.

Live/Dead Staining

Live/dead staining was performed using 5-carboxyfluorescein diacetate acetoxymethly ester, which stains live cells green, and propidium iodide, which stains dead cells red according to the manufacturer's instruction (Invitrogen). Three sets of surfaces were analyzed for each sample type.

Functional Testing

The electrical function of in vitro samples of neonatal cardiomyocytes encapsulated in chitosan hydrogels for 6 d was established by measuring excitation threshold (ET), the minimum voltage required to pace the encapsulated cells simultaneously, and maximum capture rate (MCR) as previously described, (Radisic, Park et al. 2004), the contents of which are incorporated by reference. The MCR is the maximum stimulation rate at which the encapsulated cardiomyocytes can be induced to beat simultaneously, the encapsulated samples were placed between a pair of carbon electrodes immersed in warm Tyrode solution (Sigma, pH 7.4). The ET was measured by stimulating the samples with square pulses of 2 ms width at a frequency of 1 Hz and increasing the output voltage of the stimulator until ~90% of the cells in the field-of-view were beating synchronously with the stimulator output. The MCR was measured by setting the output at 15 V, and increasing the frequency until most of the cells in the sample were no longer synchronously beating with the driving signal. All measurements were taken using bright field microscopy. The samples were placed in an environmental chamber at 37° C. for the measurements (N=3/group).

Sample Preparation for In Vivo Implantation

Cardiac constructs were made by encapsulation of neonatal Lewis rat cardiomyocytes in Az-chitosan-QHREDGS or Az-chitosan-RGDS. A total of $2 \times 10^6$ cardiomyocytes were resuspended in 15 μL of ice cold cardiomyocytes medium with 30% FBS for at least 10 min. These cells were then encapsulated in 100 μL of the hydrogel in transwell plates and constructs (2 mm thick and 6 mm in diameter) were produced. A total of 8 samples were made for each type of hydrogel, and 4 from each group were implanted, while the other 4 were retained as in vitro controls. Samples were cultured at 37° C. for 5 d before they were implanted in vivo.

Subcutaneous Implantation and Histological Assessment

Cardiac constructs described above were inserted subcutaneously into the abdomen of Lewis rats. Four samples were implanted for each type of hydrogel. Animals were observed for 7 d and then implanted tissues recovered. Histological sections of 4-5 μm were prepared from samples frozen in O.C.T. compound and stained for hematoxylin and eosin (H&E), smooth muscle actin (SMA) and Factor VIII as described, (Fujii, Sun et al. 2009), the relevant contents of which are incorporated herein by reference. Quantification of total SMA and Factor VIII was performed using ImageScope v10 (Aperio Technologies) and mean intensities were averaged for six fields for each sample and normalized to total area. Immunofluorescence staining was performed on frozen sections for cardiac sarcomeric α-actinin, and troponin I as described, (He, Chen et al.), the relevant contents of which are incorporated herein by reference. Apoptosis was assessed using a TUNEL assay (Roche Applied Science) following the manufacturer's standard protocol.

Statistical Analyses

All data are expressed as mean±S.E.M. and "n" is the number of experiments per group. Unpaired student's t tests or one-way ANOVAs were used to compare among experimental groups. Data was analyzed using Prism 4.0c (Graphpad Software, Inc.) and a p<0.05 was considered statistically significant.

Results and Discussion

Figure 5:
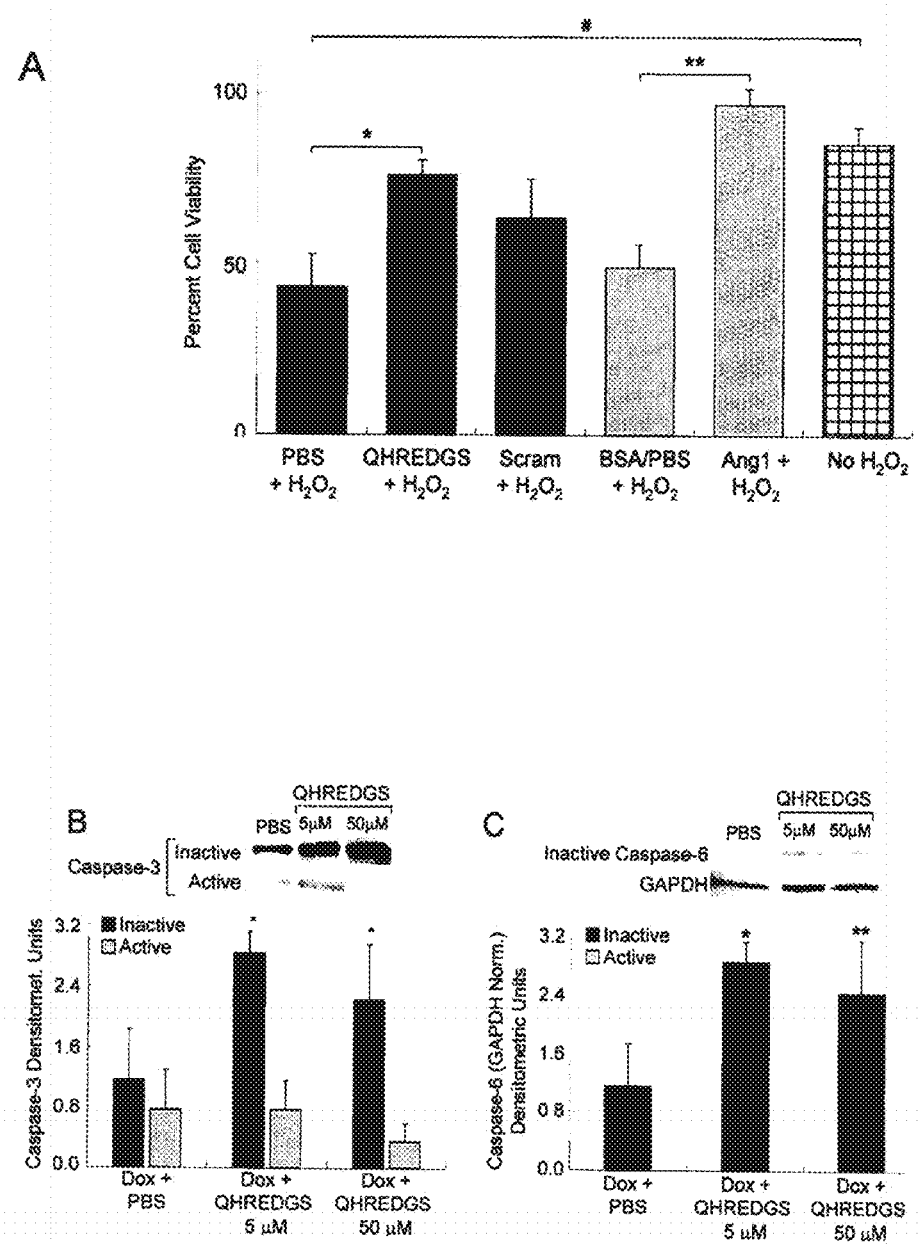
FIG. 5 graphically illustrates cardioprotective properties of QHREDGS on cardiomyocytes in monolayer during oxidative stress (A) and under conditions of induced apoptosis (B, C), as well as increasing ATP levels in serum-starved cardiomyocytes (D)
Figure 5:
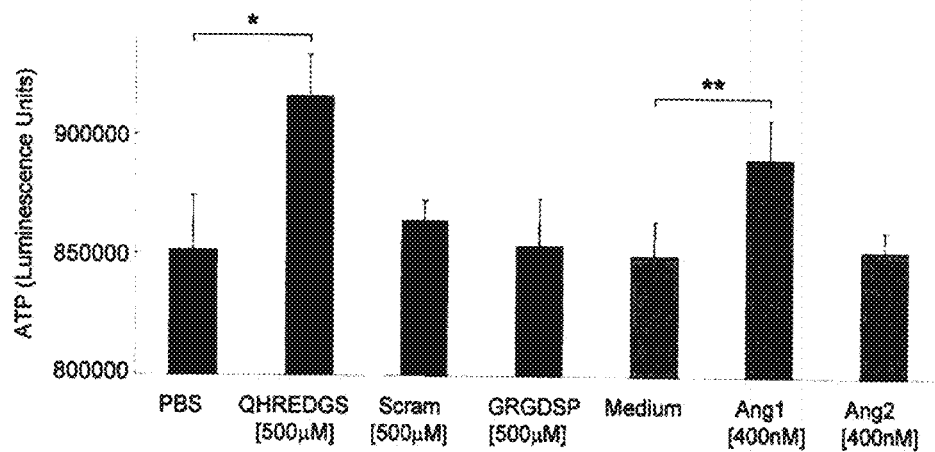

Effect of Soluble QHREDGS Peptide on Neonatal Cardiomyocytes in Monolayer Culture Superoxide burst is one of the major causes of cardiomyocyte death upon reperfison. Therefore, the ability of ang 1 and QHREDGS peptide to prevent cell death in cardiomyocytes treated with $H_2O_2$ in vitro was tested. The data show that with $H_2O_2$, cardiomyocyte viability declines to under 50% (FIG. 5A). In contrast, ang 1 and peptide QHREDGS maintain cardiomyocyte viability after exposure to $H_2O_2$. Therefore, ang 1 and QHREDGS peptide effectively protect neonatal rat cardiomyocytes against cell death and injury induced in vitro.

Doxorubicin (Dox) is another potent agent which induces apoptosis in cardiomyocytes. The ability of QHREDGS peptide to protect cardiomyocytes against Dox-induced apoptosis was evaluated by evaluating activation of caspase-3 and -6. These caspases are considered end-stage executioner caspases; however increases in their activity may not always lead to cell death. For example, a lesser amount of caspase-3 activation will not commit cells to die, but rather can cause proteolysis and degradation of cardiomyocyte contractile proteins, and thus, substantially impair myocyte contractility, which can depress cardiac function. The data clearly indicate that, activation of caspases-3 and -6 were blocked by doses of QHREDGS peptide as low as 5 µM (FIG. 5B,C). Whereas peptide free controls given doxorubicin (PBS+Dox) exhibited a significant decrease in the presence of the inactive forms of caspase-3 and 6, the groups treated with QHREDGS peptide maintained the levels of inactive caspases at comparable amounts to the doxorubicin-free controls (PBS) (FIG. 5B,C).

ATP is the leading source of energy and metabolism in cardiomyocytes, thus ATP levels are critically important for cardiac cell function. In serum-starved conditions, both QHREDGS peptide and ang 1 substantially increased cardiac myocyte ATP levels, whereas scrambled QHREDGS, RGD-based peptides, and ang2 had no such effect (FIG. 5C). Improving myocyte energetics in the adverse condition of serum-deprivation would be beneficial to attenuating the progression of cardiac injury, as occurs in cardiovascular disease.

Overall, these monolayer studies demonstrate that the QHREDGS peptide applied in the soluble form in the culture media protects cardiomyocytes against cell death inducing agents and maintains cardiomyocyte energetics.

Properties of the Peptide Modified Hydrogels

The elastic moduli of the base material, Az-chitosan, were assessed by micropipette aspiration at two concentrations (10 mg/mL and 20 mg/mL). For comparison, micropipette aspiration was also performed using neonatal and adult rat hearts. The modulus of the 20 mg/mL Az-chitosan hydrogel was significantly greater than that of the 10 mg/mL Az-chitosan hydrogel (Table 2) as expected. The moduli of the 20 mg/mL Az-chitosan samples approached that of the neonatal rat heart tissue; however, they were not as stiff as adult rat hearts (Table 2). Cardiomyocytes themselves are particularly sensitive to the physical characteristics of their surrounding environment. Scaffold stiffness has been demonstrated to affect contractility of cardiomyocytes. Cardiomyocytes cultured on stiff fibrotic-like substrates lose their spontaneous contractile activity quickly, whereas cells grown on elastic substrates mimicking cardiac tissue preserve contractility for longer time periods.

TABLE 2

Elastic moduli of Az-chitosan samples and hearts of Sprague-Dawley rats.

| Sample Type | Elastic Moduli (kPa) |
|---|---|
| Az-chitosan (10 mg/mL) | 1.9 ± 0.2 (1.7-2.0) |
| Az-chitosan (20 mg/mL) | 3.5 ± 0.6 (2.9-4.2)* |
| Neonatal Heart of Sprague-Dawley Rat[&] | 4-11.4 |
| Adult Heart of Sprague-Dawley Rat[&] | 11.9-46.2 |

N = 3-4 measurements were made per group.
[&]As reported previously (Bhana, Iyer et al.).
*Significantly higher than the 10 mg/mL gel (p < 0.01).

Azidobenzoic acid modification of chitosan, with an identical conjugation protocol, was confirmed by $^1$H NMR (see Example 1). Conjugation efficiencies of QHREDGS and the RGDS peptides to Az-chitosan were quantified using fluorescently tagged peptides. There were no significant differences in conjugation efficiencies between the two peptides. On average ~50% of the peptide added to the reaction solution was conjugated to Az-chitosan, specifically 57.6±5.8% for QHREDGS and 46.0±7.1% for RGDS (Table 3).

TABLE 3

| Peptide | Mass in reaction solution (mg) | Concentration in reaction solution (mg/mL) | Theoretical concentration post dialysis (mg/mL) | True concentration post dialysis (mg/mL) | Mass Peptide/ Mass Az-Chitosan (mg/mg) | Conjugation Efficiency |
|---|---|---|---|---|---|---|
| FITC-C6-QHREDGS | 4 | 1.33 | 1.14 | 0.66 ± 0.07 | 0.38 ± 0.04 | 57.6 ± 5.8% |
| FITC-C6-RGDS | 2 | 0.67 | 0.57 | 0.26 ± 0.04 | 0.15 ± 0.02 | 46.0 ± 7.1% |

Therefore, the molar concentration of the two different peptides per gram of Az-chitosan was comparable (Table 4).

TABLE 4

Estimated molar concentrations of peptides conjugated to Az-chitosan based on conjugation efficiencies in Table 3.

| Peptide | Mass in reaction solution (mg) | Molecular Weight (g/mol) | Concentration in reaction solution (☐mol/mL) | Number of Moles of Peptide per Mass of Chitosan (☐mol peptide/g Az-chitosan) |
|---|---|---|---|---|
| QHREDGS | 4 | 827.81 | 1.61 | 0.54 |
| RGDS | 2 | 433.42 | 1.54 | 0.41 |

Scanning electron microscopy of crosslinked chitosan hydrogels evaluated the three-dimensional surface structure of the hydrogels. Use of a cold-stage adaptor and VP SEM assisted in the preservation of surface structure and limited sublimation of frozen water. Representative images of Az-chitosan, Az-chitosan-QHREDGS, and Az-chitosan-RGDS coated glass coverslips qualitatively demonstrate the porous nature of the hydrogels. In contrast, the control glass substrate exhibited a smooth surface. Hydrogel porosity is desirable for encapsulated cells and permits sufficient nutrient and oxygen diffusion throughout the material. The Az-chitosan hydrogel possessed the highest degree of porosity, while the Az-chitosan-QHREDGS and Az-chitosan-RGDS hydrogels were slightly less porous. This is likely due to crosslinking, as the peptide-modified hydrogels may have additional EDC-induced crosslinking between peptides. However, the largest pores in peptide-modified hydrogels were 70-80 elm in diameter, thus potentially allowing cell penetration and elongation. Fiber-like structures, 3-4 µm, in diameter were also observed in all samples.

Hydrogel degradation in serum containing culture medium was assessed at 37° C. Over 11 days in vitro, there were no significant differences in percent degradation between the groups, indicating that peptide modification did not significantly affect this property (Az-chitosan: 15±37%, QHREDGS modified Az-chitosan: 19±10% and RGDS modified Az-chitosan: 17±7%, N=3 per group).

Cultivation of Cardiomyocytes Encapsulated in Chitosan Hydrogels

Cardiomyocytes were encapsulated in Az-chitosan, Az-chitosan-RGDS and Az-chitosan-QHREDGS hydrogels and crosslinked onto glass coverslips with UV light exposure. Live/dead cell staining was performed after 6 days of static cultivation to determine cell viability. Peptide-modified hydrogels contained considerably more encapsulated live cells than the Az-chitosan control. In fact, no cells were observed visibly contracting in the Az-chitosan control group, which corresponded with the observed lower cell viability. Neonatal rat cardiomyocytes in the Az-chitosan control group appeared rounded, whereas cells in peptide-conjugated hydrogels were elongated and rod-shaped.

Cells encapsulated in the peptide-modified hydrogels contracted spontaneously with large areas of synchronization. The QHREDGS peptide resulted in the formation of a dense syncytium which is critical for proper myocardial contractility, whereas only islands of connected cells were observed in the RGDS modified hydrogel. These observations confirm the ability of these peptides to promote the attachment and viability of the neonatal rat cardiomyocytes in the peptide Az-chitosan hydrogel system. These findings also confirm that the peptide-modified hydrogels possessed sufficient porosity to support cell survival in an encapsulated system over a prolonged time in culture. The small amount of hydrogel degradation during culture likely facilitated the cell linkage and syncytium formation.

During cultivation, regions of spontaneously contracting cardiomyocytes were observed in the peptide modified groups. Electrical field stimulation was employed at the end of the cultivation period to determine the functional capacity of the encapsulated neonatal rat cardiomyocytes. Similar to native heart tissue, the response of isolated cardiomyocytes to electrical stimulation is indicative of cell viability and functional capability. Cardiomyocyte contraction could not be induced following encapsulation in Az-chitosan controls. The entire constructs containing myocytes plus Az-chitosan-QHREDGS or Az-chitosan-RGDS hydrogel beat synchronously (Table 5). There were no significant differences in excitation threshold (ET), minimum voltage required to pace the encapsulated cells simultaneously, or the maximum capture rate (MCR) between the cells encapsulated in the QHREDGS versus RGDS hydrogel (Table 5). Thus, the type of peptide did not significantly affect contractile properties in this hydrogel system.

TABLE 5

Electrical excitability of encapsulated heart cells after six days of cultivation

|  | ET (V) | MCR (pps) |
|---|---|---|
| Neonatal rat heart | 3.2 ± 1.5 | 5.7 ± 1.1 |
| Cells encapsulated in Az-chitosan-QHREDGS | 7.0 ± 0.4; 9.2 ± 0.6 | 4.3 ± 0.1 |
| Cells encapsulated in Az-chitosan-RGDS | 7.5 ± 0.7; 9.3 ± 0.5 | 4.1 ± 0.5 |

ET—excitation threshold; V—volts; MCR—maximum capture rate; pps—pulses per second The recordings obtained from the electrical stimulation experiments show that encapsulated neonatal cardiomyocytes can respond to external electrical stimulation. The MCR was slightly reduced in the peptide-conjugated hydrogels compared to native heart. Following the isolation of neonatal cardiomyocytes and their hydrogel encapsulation, cell viability ranged from 50-70%, and therefore dead cells were also encapsulated and trapped in the system. Dead cells do not efficiently propagate electrical signals, thereby adversely affecting the functional parameters measured during this study.

Subcutaneous Implantation/In Vivo Assessment of Cardiomyocyte/Hydrogel Constructs To assess the in vivo response, cardiomyocyte/hydrogel (Az-chitosan-RGDS or Az-chitosan-QHREDGS) constructs were implanted after 5 days of in vitro cultivation. Immunocompetent syngeneic Lewis rats were selected as cell donors and implant recipients to enable the full evaluation of the in vivo host response. The animals were healthy upon completion of the study (7 days post-implantation), and showed no external signs of inflammation. Upon retrieval of the constructs, no spontaneous contractions of the nodules were observed.

For in vivo studies, the presence of cells that are involved in angiogenesis [endothelial cells (Factor VIII positive)] and wound healing [myofibroblasts/smooth muscle cells (SMA positive)] were assessed as well as cardiomyocytes (troponin I positive and sarcomeric α-actinin positive).

H&E staining qualitatively examined biomaterial degradation and tissue morphology, including the presence of encapsulated cells and additional autologous cell infiltration. Representative images showed cell nuclei stained blue and cytoplasm stained light pink. The Az-chitosan hydrogels appear dark red in both images. Cells were located throughout the biomaterial in both groups, mainly attached to the hydrogel pores and occasionally spanned the pores. On day 7, the hydrogels appeared to be largely intact, as evidenced by the presence of the large amount of dark red porous structures. The RGDS-conjugated Az-chitosan group appeared to have undergone a slightly greater degree of degradation due to cell infiltration as indicated by densely packed blue nuclei. The QHREDGS-conjugated hydrogel had less cell infiltration, suggesting little to no immune reaction against the implanted constructs.

The QHREDGS-conjugated hydrogels have a reduced inflammatory infiltrate similar to the full length parent protein, ang 1.

Histological staining for SMA was also conducted to assess whether fibrosis occurred in the samples following implantation. In these sections, SMA-positive tissue stained dark brown and cell nuclei stained blue. The SMA-positive staining was limited and diffuse in irregular patterns throughout the nodules. However, signs of significant fibrosis such as fibrotic encapsulation of the entire implant were absent. This staining pattern is consistent with the presence of myofibroblasts. The presence of myofibroblasts in the Az-chitosan-QHREDGS hydrogel is consistent with the reparative process.

Staining for Factor VIII was performed to identify blood vessel formation within the constructs. Endothelial cells, which line blood vessels, are stained brown by Factor VIII. In 7 days, it was not sufficient time to identify distinct blood vessels within the nodules. Similar extents of Factor VIII staining were found between the two peptide groups, indicating that RGDS and QHREDGS peptides do not differ significantly in endothelial cell recruitment to the host.

To specifically identify and characterize cardiomyocytes within the hydrogel nodules, immunofluorescence staining using the cardiac-specific markers sarcomeric α-actinin and cardiac troponin I was conducted. Proteins of interest were stained green and nuclei were stained blue. These cytosolic proteins exhibit distinct patterns and highlight the contractile apparatus of cardiomyocytes. Remarkably, the Az-chitosan QHREDGS-conjugated hydrogel possessed larger areas of cardiomyocytes compared to the RGDS-conjugated controls. Areas of healthy, elongated cardiomyocytes were observed, whereas the RGDS-conjugated hydrogel contained only round immature cardiomyocytes with limited cardiac-specific staining patterns. These findings indicate that the QHREDGS peptide was considerably better than the RGDS peptide in promoting the maturation of a differentiated cardiomyocyte phenotype in the setting of cell/hydrogel transplantation. As the hydrogels began to degrade, the encapsulated cell clusters not only maintained their contractile apparatus, but the clusters seemed to coalesce to form a syncytium. Cardiomyocytes were not beating at 7 days post-implantation Since the majority of cell death occurs early after construct implantation, while the implant is still not fully vascularized, the experiment was terminated at 7 days after implantation. TUNEL staining indicated significantly fewer apoptotic cells in the QHREDGS modified hydrogel compared to the RGDS peptide modified Az-chitosan. In addition, double staining for cardiac troponin I and TUNEL indicated fewer apoptotic cardiomyocytes in the QHREDGS modified hydrogel compared to the RGDS modified hydrogel implanted sub-cutaneously. The data indicate that the percentage of apoptotic cells was three times lower in the QHREDGS group (~1.5%) versus the RGDS group (~4.5%).

Conclusions

The QHREDGS peptide covalently bound to the non-cell adhesive Az-chitosan hydrogel promoted attachment and viability of encapsulated cells during in vitro cultivation at similar levels as the RGDS peptide. Upon in vivo implantation, the QHREDGS peptide attenuated apoptosis better than RGDS peptide covalently bound to Az-chitosan hydrogel, yielding more healthy cardiomyocytes in implants. Further, the QHREDGS peptide promoted elongation and assembly of contractile structures. Az-chitosan-QHREDGS gel had a significantly higher percentage of SMA+ myofibroblasts compared to the Az-chitosan-RGDS hydrogel.

Example 3

Rat Myocardial Infarction Model

Methods

All animal experimental procedures were approved by the Animal Care Committee of the Toronto General Research Institute and the University of Toronto Committee on Animal Care, according to the Guide for the Care and Use of Laboratory Animals.

Conjugation of QHREDGS Peptide to Chitosan

QHREDGS peptide was conjugated to chitosan using 1-ethyl-3-(-3-dimethylaminopropyl) carbodiimide HCl (EDC) chemistry in a manner similar to that previously described Rask et al., J Biomed Mater Res A, 2010. 95(1): p. 105-17, the relevant contents of which are incorporated herein by reference. Briefly, chitosan (UP-G113, Novamatrix) was dissolved at 20 mg/mL in 0.9% normal saline and peptide at 10 mg/mL in phosphate buffered saline (PBS, Lonza). These were then mixed with EDC and N-hydroxysulfosuccinimide (S—NHS), dissolved in PBS, to obtain a final reaction solution of 5 mg/mL chitosan, 3 mg/mL QHREDGS peptide, 2.4 mg/mL EDC, and 6.6 mg/mL S—NHS. The reaction solution (1.5 ml) was then left on a vortex mixer (VWR) at 650 RPM for 3 hours, diluted 4× with PBS and dialysed (using a dialysis membrane, Spectra/POR MWCO 3500, Spectrum Labs) against two 2 L changes of distilled water for ~24 hours. The dialyzed solution was then passed through a 0.2 µm syringe filter (Progene), recovered through lyophilisation for 48 hours and stored at −20° C. until use.

Hydrogel Formulation

The 2.5 mg/mL 1:1 chitosan-collagen hydrogel formulation consisted of 203.1 µL pure (Control gel) or peptide-modified chitosan (dissolved in sterile 0.9% normal saline at 12.31 mg/mL;) mixed with 100 µL 10×PBS, 681.2 µL of 3.67 mg/mL collagen (BD Biosciences), and 15.7 µL 1N NaOH on ice, in that order to make 1 mL of gel solution. The final hydrogel solution, with chitosan (or peptide modified chitosan (QHG213H)) concentration of 2.5 mg/mL and collagen concentration of 2.5 mg/mL, was mixed thoroughly and kept on ice until needed.

Rat LAD MI Model

Adult male Lewis rats were submitted to a left ventricular anterior descending coronary artery ligation procedure (LAD procedure) to mimic acute MI. Animals were divided into five groups: Sham, MI Only, Control gel, Thymosin β-4 (Tβ4) gel and peptide modified QHG213H gel. The final concentrations of collagen I, chitosan and Tβ4 were 2.5 mg/mL, 1.25 mg/mL (Control group) and 30 µg/mL Thymosin β4 for Tβ4. For the QHG213H gel peptide conjugation efficiency quantification with fluorescently labelled peptides demonstrated 0.35 mg QHREDGS/ml of hydrogel solution. Briefly, animals were initially anaesthetized with 5% isoflurane and maintained with 2-2.5% isoflurane during surgery. Animals were intubated and ventilated using a Minivent ventilator (Harvard Apparatus, March—Hugstetten, Germany) at ~200 breaths/min. A left thoracotomy was performed, and the left coronary artery was ligated using a 7-0 silk suture (Ethicon) passed with a reverse cutting needle. Sham rats did not receive the LAD ligation and the chest was closed immediately. Test groups had a total of 50 µL of appropriate (Control, Tβ4, or QHG213H) gel injected with a 27½ G needle into the area immediately below the ligation suture in three injections. In all cases, the hydrogel was warmed to ~37° C. for ~10 min prior to injection to allow gelling to initiate. The animals were removed from the ventilator and allowed to recover below a heat lamp for approximately 30 minutes.

Rats were housed for three weeks and then sacrificed through anaesthetization with 5% isoflurane followed by cervical dislocation. Hearts were excised, washed with PBS, and fixed for ~24 hrs with 10% formalin. Excess tissue was cleaned, hearts were imaged, sectioned in two locations just below the LAD suture location, and finally sections were imaged. These feasibility studies included N=2 animals for Sham and MI Only groups, N=3 for Control Gel, Tβ4, and QHG213H gel groups.

Histological Staining

Fixed heart sections were sent for paraffin embedding and immunohistochemical staining at the Pathology Research Program (PRP) at the University Health Network. Paraffin embedded sections were stained for haematoxylin & eosin (H&E), factor VII (F8), smooth muscle actin (SMA), cluster of differentiation (CD31), and Mason's trichrome (A). Chitosan staining was performed using Cibracon Brilliant Red-3BA (CBR-3BA, Sigma Aldrich) and Weigert's Iron Hematoxylin.

Imaging & Quantification

Whole hearts, sections, and trichrome stained sections were imaged using an Olympus SZ61 microscope mounted with an Olympus SC30 digital camera and Olympus cellSens Dimension v1.41 imaging software. F8, SMA, CD31, and chitosan stained sections were imaged using an Olympus CKX41 microscope mounted with an Olympus SC30 digital camera and Olympus cellSens Dimension v1.41 imaging software. All measurements were done using Olympus cellSens Dimension v1.41 software and Adobe Photoshop CS3.

Statistical Analysis

Statistical analysis was performed using SPSS Statistics 17.0 and GraphPad Prism 5.0. Differences between experimental groups were analyzed using one-way ANOVA with post-hoc Tukey tests or two-way ANOVA with Bonferroni post-tests. P<0.05 was considered significant for all statistical tests. Results were plotted with GraphPad Prism 5.0, with all data being reported as mean±standard deviation.

Results

Three weeks post LAD surgery the rat hearts were collected and the site of infarct identified as the area directly below the ligation suture. It was immediately clear that the MI Only, Control, and Tf34 gel hearts appeared more dilated in comparison to the control Sham operated animals, while the QHG213 gel injected hearts appeared similar in size to the Sham hearts. Sham animals did not receive an MI, instead the chest was simply open and closed. Tissue cross-sections encompassing the MI area demonstrated pathological remodelling that occurs post MI, with MI Only, Control and Tβ4 gel groups showing significant tissue loss and collagenous scar tissue deposition. Surprisingly, the QHG213H injected hearts showed very little tissue loss and minimal collagenous scar tissue deposition, appearing very similar to Sham hearts. Chitosan staining done on paraffin embedded cross-sections was performed to assess the presence of hydrogel at the injection site in the infarct area and was confirmed in the QHG213H group only. This does not exclude Control and Tβ4 gel groups from properly gelling in the infarct zone as it is possible they have simply fully degraded at three weeks.

Figure 6:
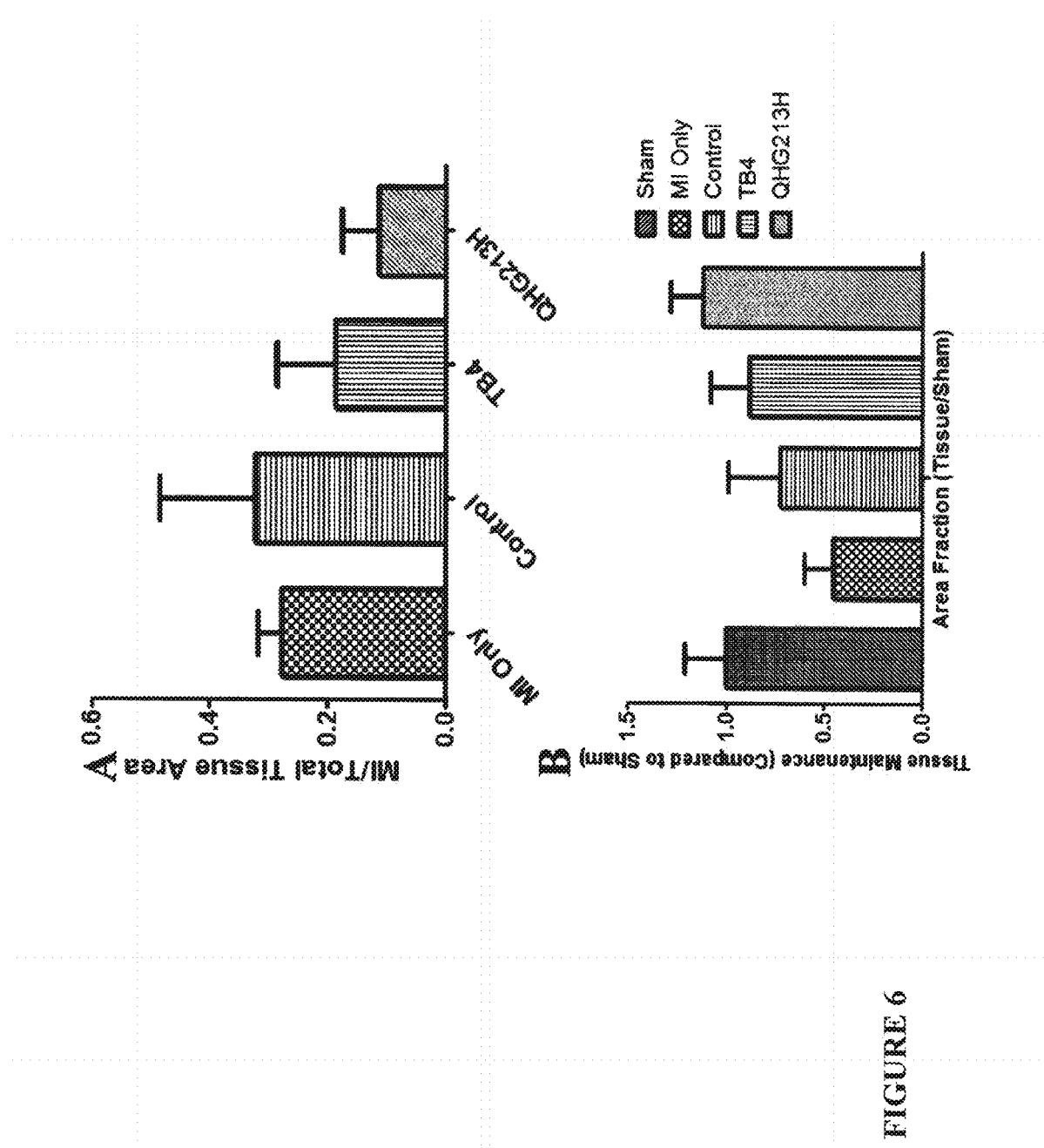
FIG. 6 graphically illustrates the effect of QHREDGS on cardiac scar tissue coverage (A) & tissue maintenance (B) in an MI model 3 weeks after injection.

Scar tissue coverage was measured by determining the area of MI and dividing by total heart tissue area from trichrome stained sections. Note RV cavity was left out of area determination. A clear trend indicating smaller infarct size compared to total tissue area with MI Only and Control gel groups showing the highest fraction, and QHG213H gel group the lowest as shown in FIG. 6A. Tissue maintenance was quantified by measuring total tissue area of all groups and normalizing to that of Sham (healthy) hearts. The QHG213H injected hearts maintained 100% tissue compared to Sham hearts, and MI Only groups maintained only ~50% as shown in FIG. 6B. N=3 per group Control gel, Tβ4 gel, QHG213-H gel; N=2 Sham & MI Only. Data reported as Mean±SD.

Figure 7:
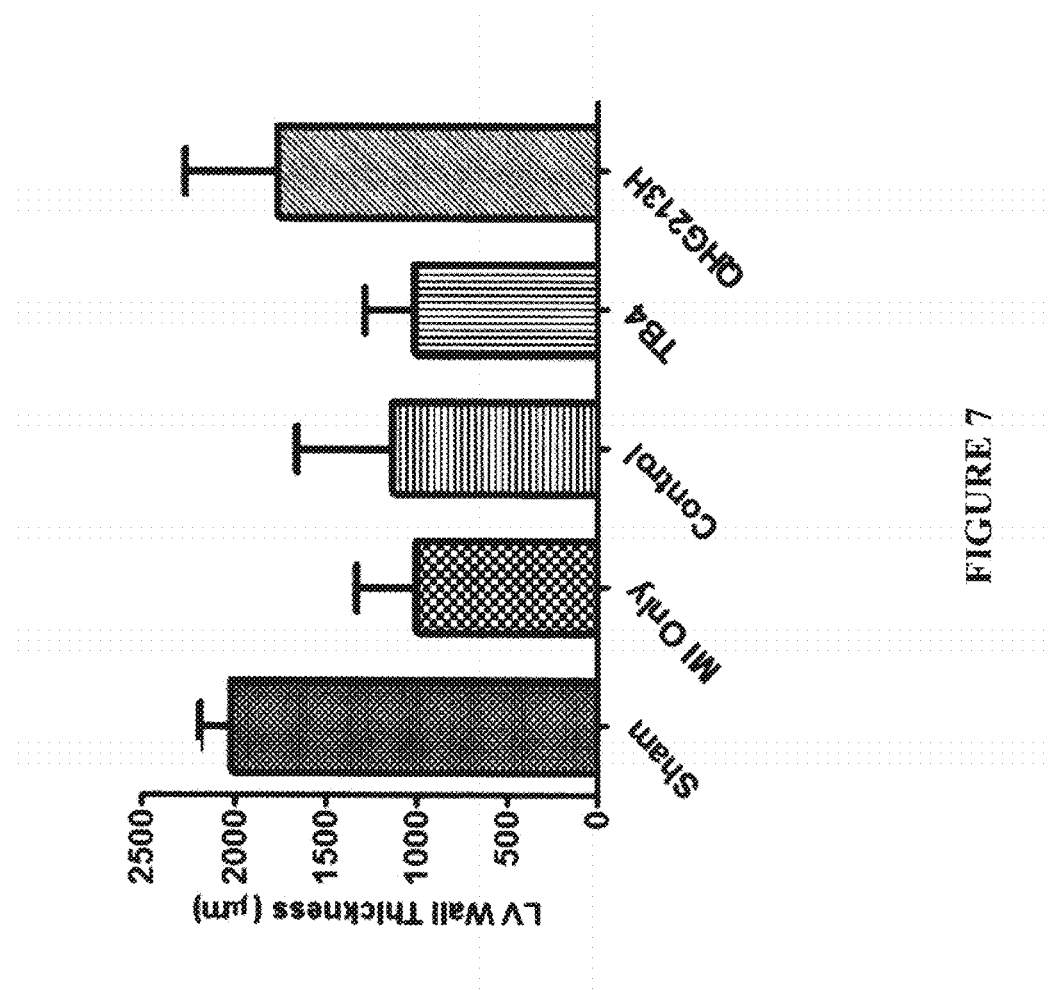
FIG. 7 graphically illustrates the effect of QHREDGS treatment on LV wall thickness in an MI model 3 weeks after injection.

Wall thickness was measured from multiple points along the MI zone for treated hearts, or along the LV for Sham hearts. MI Only, Control, & Tβ4 all showed similar MI zone wall thickness, amounting to about 50% of normal (Sham) LV wall thickness, and QHG213H group maintained almost 100% of healthy LV wall thickness as shown in FIG. 7. N=3 per group Control gel, Tβ4 gel, QHG213-H gel; N=2 Sham & MI Only. Data reported as Mean±SD.

Figure 8:
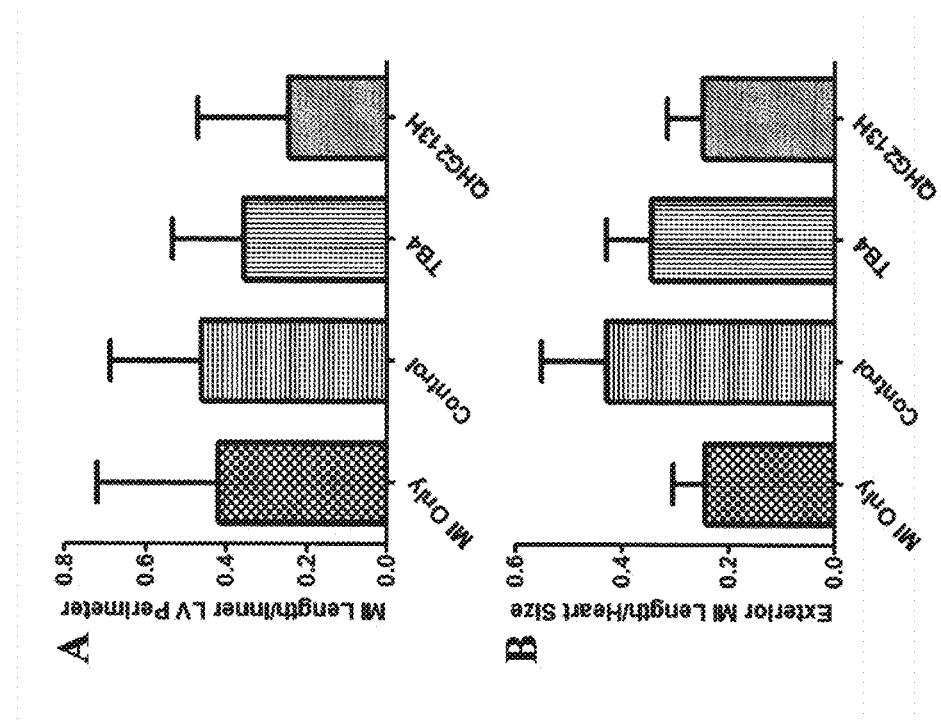
FIG. 8 graphically illustrates the effect of QHREDGS treatment on interior (A) and exterior (B) MI coverage.

Interior MI coverage was quantified by measuring the inner LV scar length compared to the overall inner LV length (cavity perimeter) measured from trichrome stained heart sections. Directly comparing each of the groups shows that QHG213H treatment yielded the best results (FIG. 8A). Exterior MI coverage was quantified in a similar fashion, measuring scar coverage on the exterior of heart sections and comparing to overall heart size (perimeter). A clear trend is seen between Control, Tβ4, and QHG213H groups with the latter showing the lowest scar coverage fraction (FIG. 8B). N=3 per group Control gel, T34 gel, QHG213-H gel; N=2 Sham & MI Only. Data reported as Mean±SD.

Figure 9:
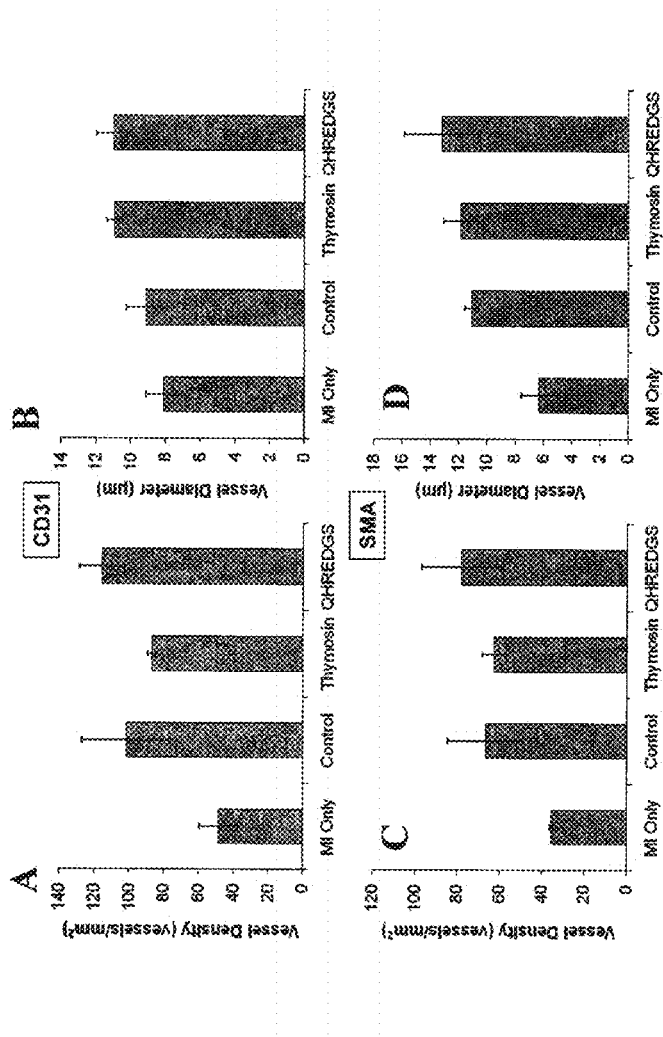
FIG. 9 graphically illustrates the effect of QHREDGS treatment on blood vessel density and blood vessel diameter in an MI model 3 weeks after injection based on CD31 (A) and SMA staining (B)

Immature vasculature and infiltration of SMA expressing cells, was identified by F8 & CD31, and SMA staining, respectively. The most pronounced difference was identified in the amount of SMA-expressing cells present, most likely reparative myoblasts, in comparison to the Sham group, with the QHG213 group showing strong expression within the identified gel nodule. Quantification of LV blood vessel diameter and density showed a trend toward higher blood vessel density and blood vessel diameter, especially with SMA staining in the QHG213 group compared to the MI only group (FIG. 9).

The results demonstrate the ability of the QHREDGS peptide to attenuate pathological remodelling process post-MI in rats. The peptide was conjugated to a hydrogel in order to ensure efficient delivery and localization of the peptide to the peri-infarct and the infarct zone; however, hydrogel-free formulations may be suitable for either systemic delivery or localized delivery to the heart. Four different controls were used for these studies in order to evaluate the effects of the QHREDGS peptide. These include: MI only controls, where infracts are induced in animals but no treatment is given; Sham controls where the chest is open and closed; Hydrogel only control where peptide-free hydrogel carrier is used; and Thymosin β4 control. Thymosin β4 is also a peptide just like QHREDGS and its cardiac regenerative potential has been demonstrated in several high impact studies. Tβ4 is an important angiogenic and cardioprotective peptide used for inhibiting myocardial cell death, inducing vessel growth, and activating endogenous cardiac progenitors. It is the first known molecule that is capable of initiating myocardial and vascular regeneration in vivo simultaneously. The present chitosan-collagen hydrogels enable controlled release of Tβ4 at nearly zero order kinetics. In addition, hydrogels with QHREDGS peptide were superior to the peptide-free controls in attenuating pathological remodeling of the heart and likely better than the state-of the art peptide Tβ4.

Example 4

QHREDGS Enhances Viability of Human iPS Cells

Materials and Methods

Maintenance Culture of Human iPS Cells.

The human iPS cells (BJ1D and 0901B) were obtained from the Ontario iPSC Facility and used following the hiPS cell research guidelines of the University of Toronto as described by Hotta et al. *Nat. Protoc.* 4, 1828-1844 (2009)), unless specified otherwise. Cells were cultured on a feeder layer of MEF cells (Mount Sinai Hospital Toronto, inactivated with 10 µg/ml mitomycin C and seeded at $1.8 \times 10^5$ per 3.5 cm dish). For single cell cultures, hiPS cell colonies were dissociated in 0.25% Trypsin-EDTA (Invitrogen) for 5 min, followed by trituration with a pipette. To ensure a single-cell suspension, the dissociated cells were passed through a 40 µm cell strainer (BD Falcon) and seeded onto MEF plates at 10 cells/ml, 10 cm plates. Cells were allowed to grow for 7 days and the total number of colonies was counted. In the treated groups, QHREDGS (Biomatik) or DGQESHR (Biomatik) dissolved in PBS (Lonza), were added at the reported concentrations to culture media at the onset of the first treatment passage and replenished with each media change. Media was changed by 100% every day. Peptides and controls were included during dissociation and passaging. Cells were analyzed after 5 passages in continuous treatment with 50 µM QHREDGS, 50 µM DGQESHR, or PBS, unless specified otherwise.

Human IPS Cell Differentiation.

Following 5 passages in continuous treatment, iPS cells were collected and differentiated into embryoid bodies (EB) containing cells of all three germ layers as described Itskovitz-Eldor, J. et al. *Mol. Med.* 6, 88-95 (2000). For further differentiation and analysis, EBs were plated onto 0.2% gelatin coated plates for another 10 days for attachment and fixed in 4% para-formaldehyde (Sigma) for immunohistochemistry.

FACS Analyses.

Analytical flow cytometry was performed on a FACSCalibur flow cytometer (BD Biosciences) as described in Chiang et al. *Acta Biomater.* 6, 1904-1916 (2010), with an additional permeabilization step with 0.25% Triton-X (Sigma) for 10 min at 4° C. Oct4 (Millipore), SSEA-4 (Developmental Studies Hybridoma Bank) and Ki67 (Millipore) and all secondary antibodies (Jackson ImmunoResearch) were used at 1:100.

BrdU Assay.

After 5 passages in treatment, human iPS cells were passaged as described above in the presence of 50 µM QHREDGS, 50 µM DGQESHR (Biomatik), or PBS (Lonza) onto MEF plates and grown for 3 days. Cultures were pulsed for 1 hr with 10 µM BrdU (Sigma) and immediately analyzed for immunohistochemistry (see below). Ki67 (Millipore, 1:300) co-staining was used to differentiate MEFs from human iPS cells. All samples were counterstained with DAPI (300 nM, Sigma).

Live/Dead, TUNEL, and Immunohistochemistry.

Human iPS cells were treated for 5 passages and stained for CFDA-Live/PI-Dead as described in Rask et al. *J. Biomed. Mater. Res. A.* 95, 105-117 (2010). Live cells were counted using the cell counter plug in for ImageJ Immunohistochemistry was performed as described above (Rask et al., ibid). Cells were fixed in 4% paraformaldehyde (Sigma) and the following primary antibodies were used: Oct4 (Millipore, 1:500), SSEA-4 (Developmental Studies Hybridoma Bank, 1:300), Ki67 (Millipore, 1:300), SMA (Sigma, 1:200), Gata6 (Millipore, 1:300), and β-III Tubulin (Invitrogen, 1:100), anti-BrdU (Abcam, 1:300). All secondary antibodies were obtained from Jackson ImmunoResearch and used at 1:200 dilutions. DAPI counterstain (Sigma) was used at 300 nM. TUNEL assay was performed as described in Rask et al. (*J. Biomed. Mater. Res. A.* 95, 105-117 (2010)) using the In Situ Cell Death Detection Kit, Fluorescein (Roche) according to manufacturer's instructions.

Apoptosis and Caspase 3/7 Activation.

Human iPS cells were treated for 5 passages and levels of apoptosis were measured 3 days after passaging using the Apo-ONE Homogeneous Caspase assay (Promega) according to manufacturers instructions. The levels of Caspase 3/7 activation were proportional to levels of fluorescence. All statistical analyses were performed using the two-tailed student t-test assuming unequal variance. $p<0.05$ denote statistical significance.

Results

Figure 10:
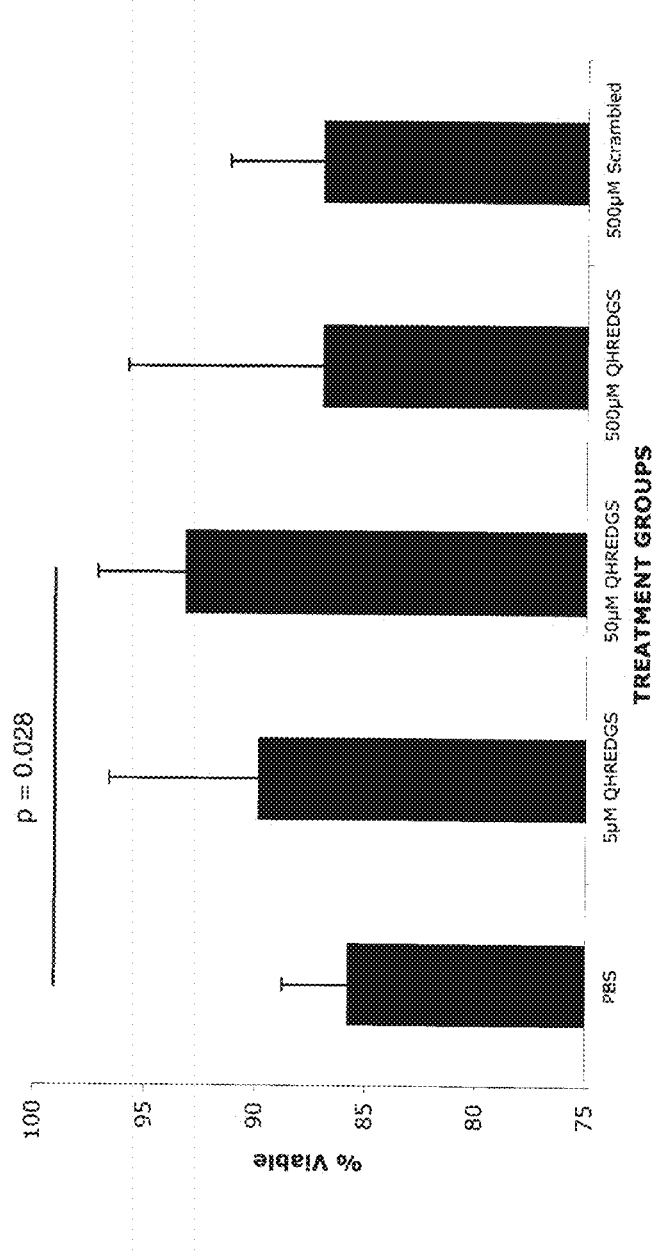
FIG. 10 graphically illustrates the effect of QHREDGS treatment on iPSC viability.
Figure 11:
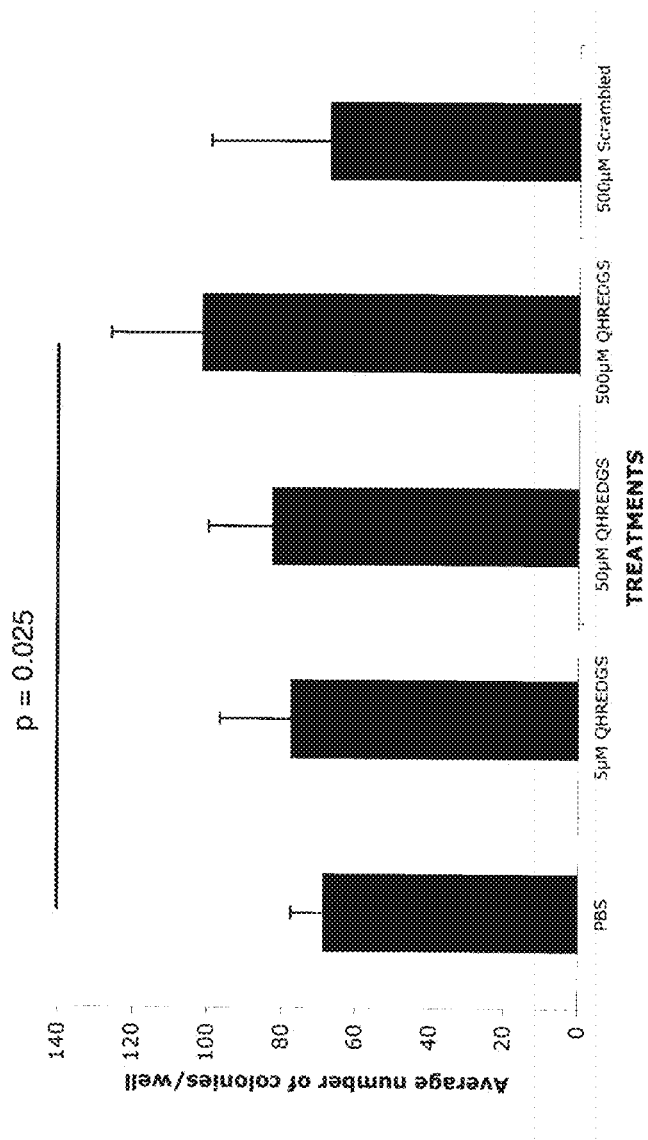
FIG. 11 graphically illustrates the effect of QHREDGS treatment on iPSC colony number following 1 passage.

To determine the optimal concentration of QHREDGS for iPSC expansion, a dose-response experiment was performed. Cells were treated with 5 µM, 50 µM, or 500 µM of QHREDGS peptide, or 500 µM scrambled peptide (DGQESHR) in PBS with a PBS treated control for five passages and stained for CFDA-Live/PI-Dead. Live cells were counted using the cell counter plug in for ImageJ. It was determined that 50 µM of soluble QHREDGS, added directly to culture medium with each media change, resulted in a significant increase ($p=0.028$) in the number of viable human iPS cells following each passage (FIG. 10, Passage 5 for cell line BJ1D) as well as an increase of greater than 10 colonies/well on average (14.3%) in the 50 µM QHREDGS treated group and a 40% increase in the 500 µM treated group compared to the PBS control (FIG. 11).

Figure 12:
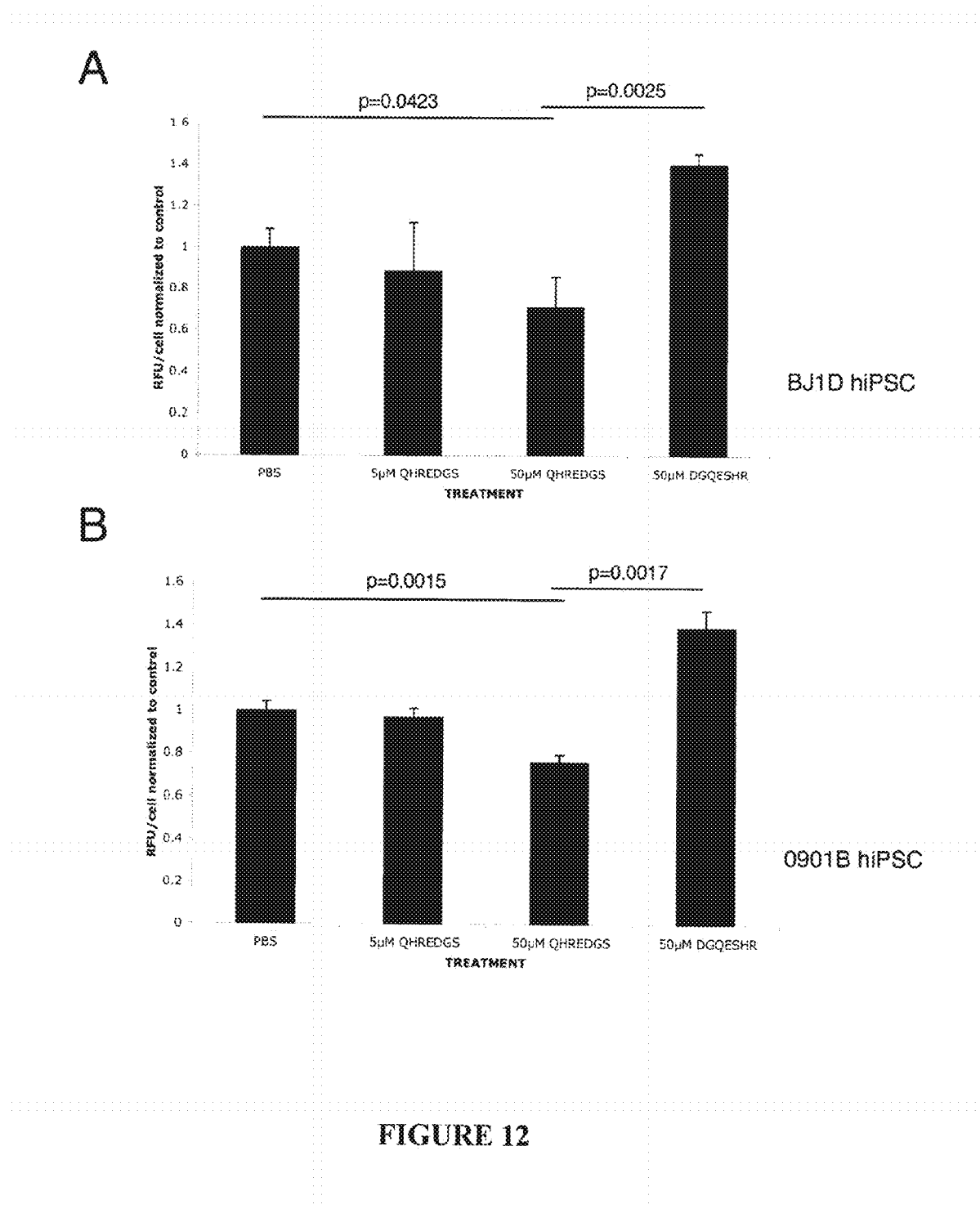
FIG. 12 graphically illustrates the effect of QHREDGS treatment on BJ1D (A) and 0901B (B) iPSC apoptosis (caspase 3/7 activity/cell number)

IPS cells, BJ1D or 0901B, were treated with 5 µM or 50 µM of QHREDGS peptide, or 50 µM DGQESHR scrambled peptide in PBS with a PBS treated control for five passages and assayed for apoptosis using the APO One Caspase 3/7 system. The levels of Caspase 3/7 activation are proportional to fluorescence. The 50 µM QHREDGS treatment significantly prevented apoptosis in human iPSCs, apparent by the significant reduction of Caspase 3/7 activity in the cells as compared to Caspase 3/7 activity of the PBS control ($p=0.0423$ for BJ1D, $p=0.0015$ for 0901B) and treatment with scrambled peptide ($p=0.0025$ for BJ1D, $p=0.0017$ for 0901B) (FIG. 12A, BJ1D; FIG. 12B, 0901B). Solid bars represent a statistical significance, $p<0.05$.

Human iPSCs undergo substantial cell death especially after complete dissociation, similar to their human ESC counterparts, which have a cloning efficiency of less than 1%. The cloning efficiency of human iPS cells when treated with QHREDGS was determined to ascertain whether or not this peptide can enhance survival of human iPS cells during complete dissociation.

iPS cells, BJ1D or 0901B were treated with 50 µM of QHREDGS peptide, or 50 µM DGQESHR scrambled peptide in PBS with a PBS treated control for five passages as a preparation for passage by trypsin. Cells were trypsinized and plated at a clonal density of 10 cells/ml for one week and the number of colonies were counted. Number of colonies per well increased significantly in the 50 µM QHREDGS treated group for both cell lines, $p<0.05$, $n=2$, 2 wells/n.

Passaging of iPS Cells and Colony Formation

Figure 13:
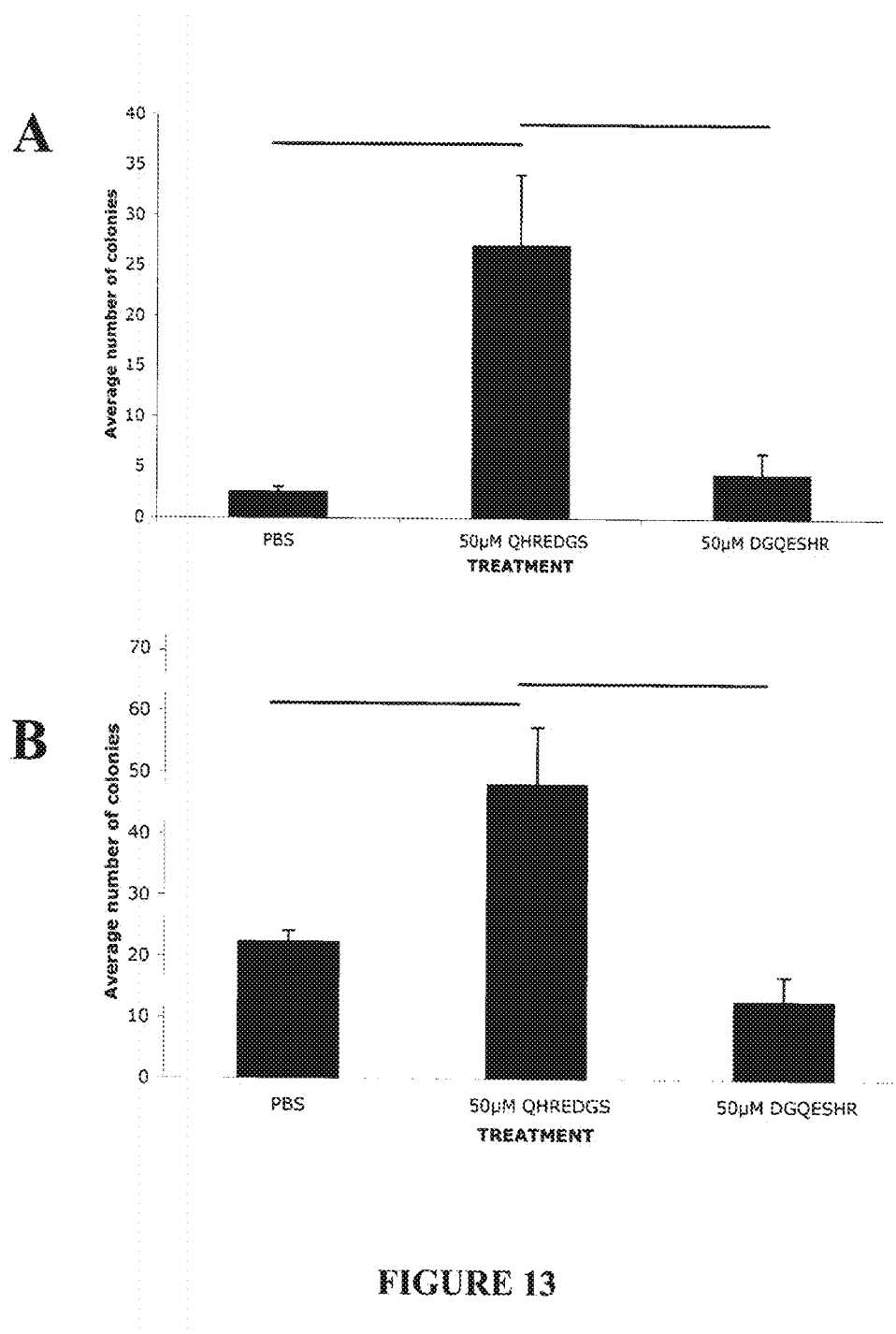
FIG. 13 graphically illustrates the effect of QHREDGS treatment on BJ1D (A) and 0901B (B) iPSC colony number following complete dissociation with trypsin, plating at clonal density and passaging.

After 5 passages in pre-treatment with 50 µM QHREDGS, or controls and complete dissociation (trypsinized), human iPS cells, BJ1D or 0901B cells, were plated on a mouse embryonic fibroblast (MEF) feeder layer at low density (100 cells/plate, 10 cm plate) in maintenance medium containing 50 µM QHREDGS, PBS, or 50 µM DGQESHR scrambled peptide. After one-week in culture, untreated or DGQESHR (scrambled peptide) treated groups generated few colonies, whereas QHREDGS treated groups for both BJ1D or 0901B cells produced many large colonies (~15 times more than the controls) (see FIG. 13A/B, respectively). The colonies were positive for Oct4, a marker for the undifferentiated state. The cloning efficiency, based on ratio of Oct4+ colonies formed per initially seeded human iPS cells, was 27+/−7.1% and 2.5+/−0.6% for BJ1D and 48+/−9.4% and 22.3+/−1.9 for 0901B in the presence and absence of QHREDGS, respectively. These efficiencies are comparable to those obtained by treatment with the widely-used Y-27632 ROCK inhibitor.

Thus, treatment with QHREDGS supports single-cell culture of human iPS cells through the promotion of colony formation.

Pluripotency and Differentiation Potential

Figure 14:
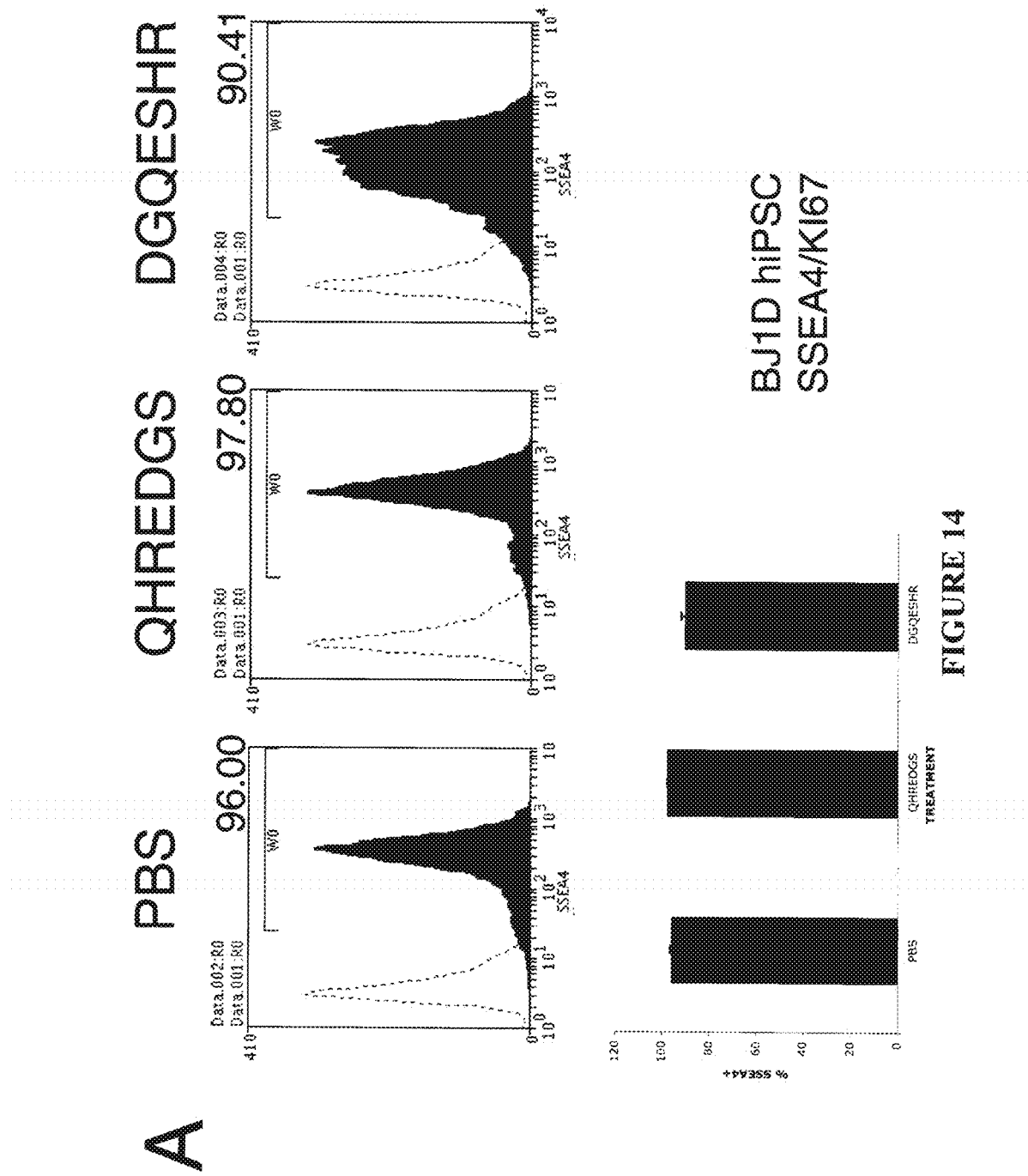
FIG. 14 A/B graphically illustrates the effect of QHREDGS treatment on pluripotency of BJ1D iPS cells.
Figure 14:
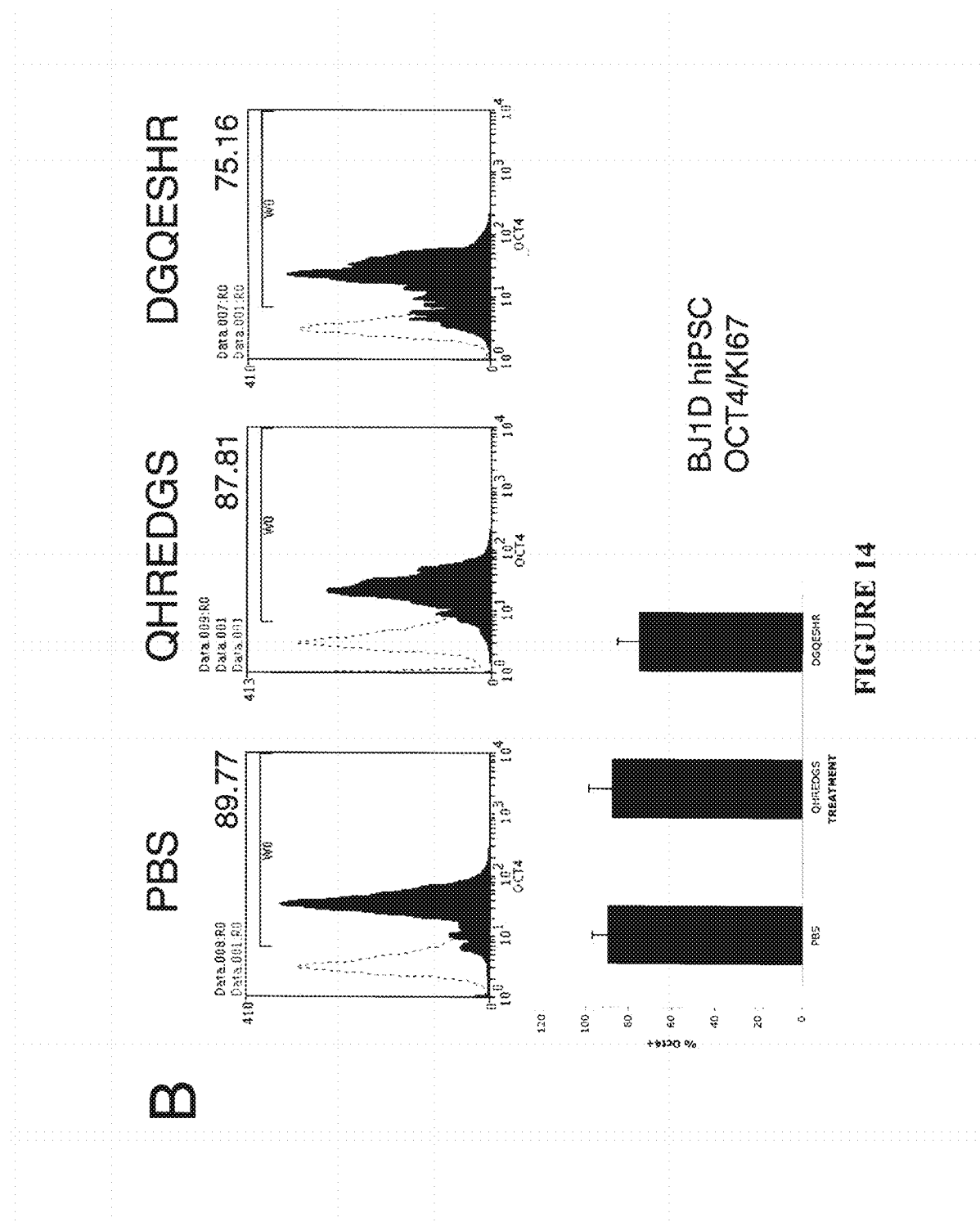
Figure 15:
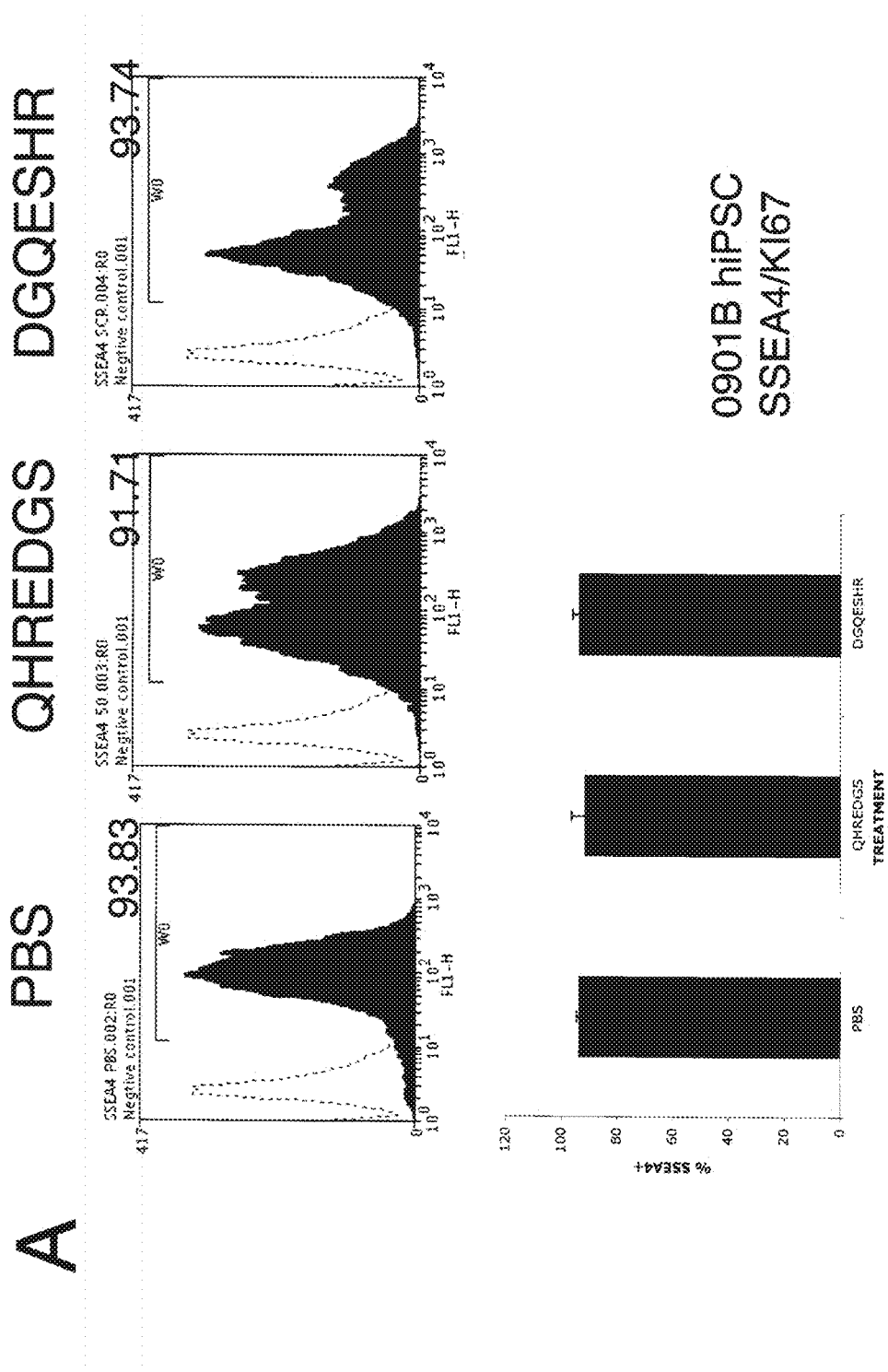
FIG. 15 A/B graphically illustrates the effect of QHREDGS treatment on pluripotency of 0901B iPS cells.
Figure 15:
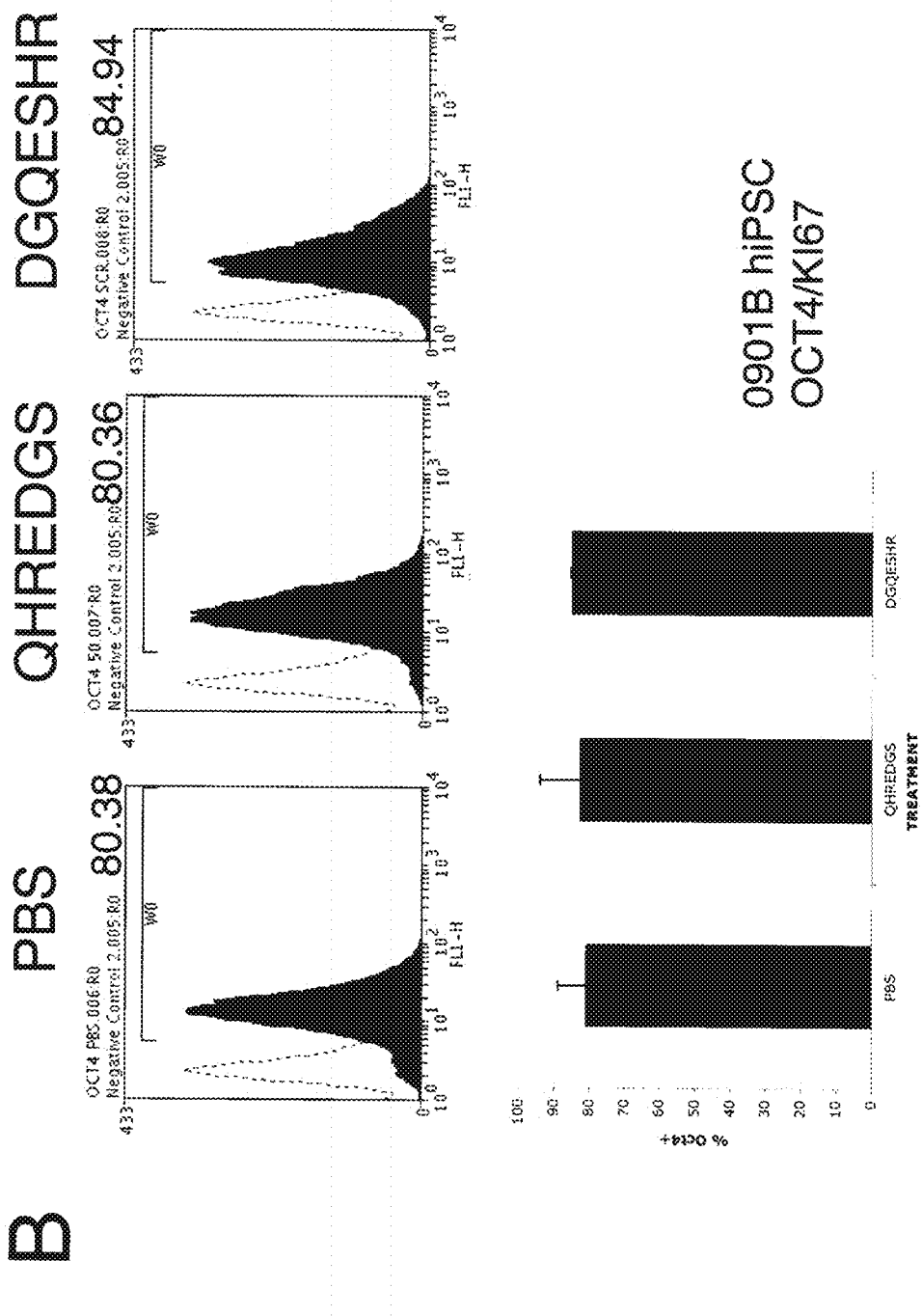

Following five passages, QHREDGS (50 μM) treated human iPS cells continue to express the undifferentiated-state markers, Oct4 and SSEA4 by immuno-histochemistry, as well as Oct4, Nanog, and Sox2 by RT-PCR. FACS analysis of Oct4+ cells as well as SSEA4+ cells indicate that QHREDGS-treated BJ1D (FIG. 14) and 0901B (FIG. 15) cells exhibit high levels of expression of Oct4 and SSEA4 that were comparable to both PBS and DGQESHR scrambled peptide controls, without any significant differences (p>0.05) indicating maintenance of pluripotency. Furthermore, treated cells after 5 passages still retained the competence to differentiate into neural cells, mesodermal cells and endodermal cells in vitro following standard EB differentiation protocols, and continued to express markers of all germ layers, i.e. Pax6 (ectoderm), AFP (endoderm), Brachuyry and CDX (mesoderm) as determined by RT-PCR.

Following 10 passages in the presence of QHREDGS (50 μM), cells continued to form teratomas after being grafted into hind-limb muscles of immunodeficient NOD-SCID mice, indicating that prolonged exposure to QHREDGS peptide does not alter the pluripotent nature of human iPS cells, and can reduce the extent of chromosomal anomalies usually present after long-term culture in vitro.

Effect of QHREDGS on iPS Cell Proliferation

Figure 16:
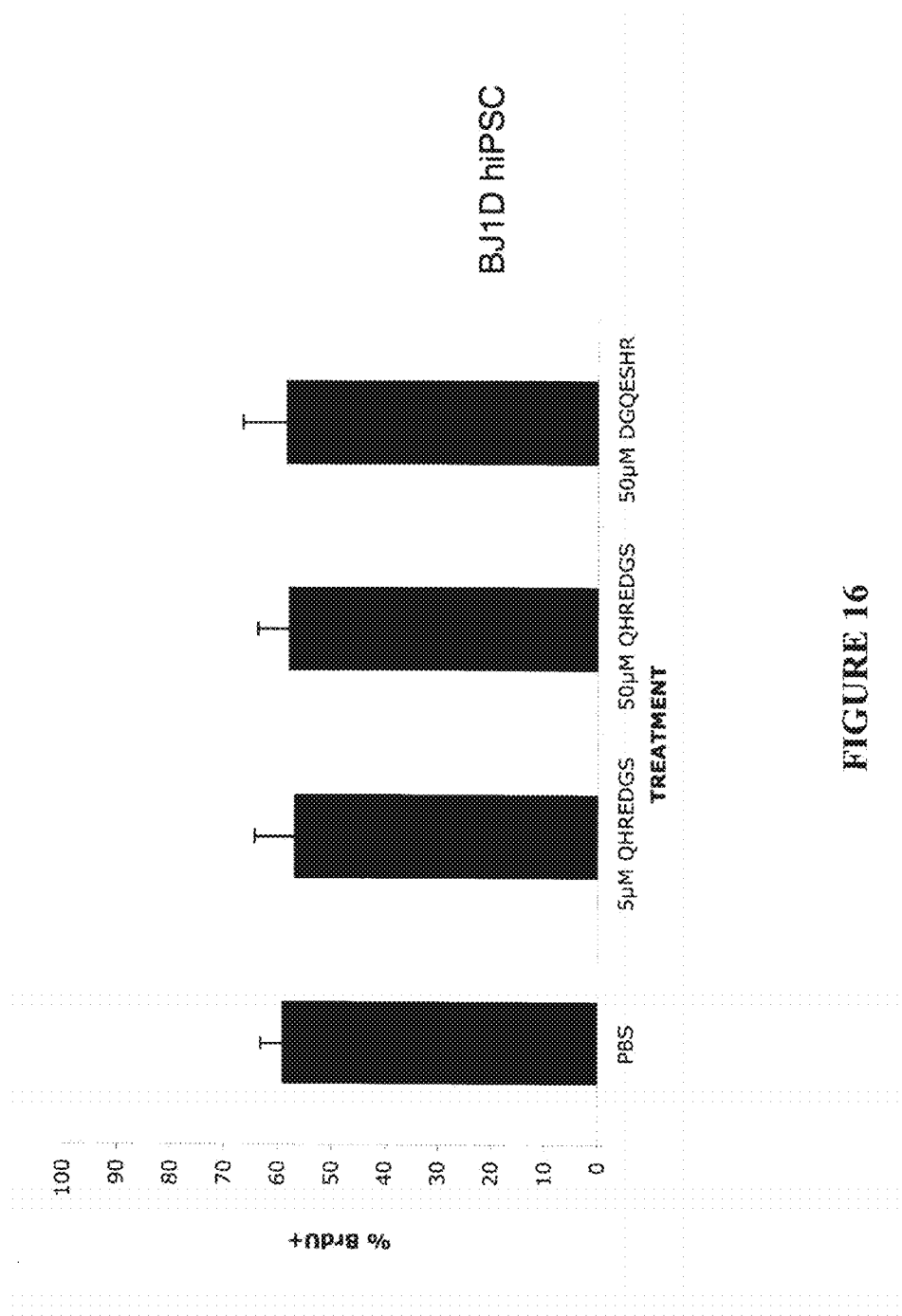
FIG. 16 graphically illustrates the effect of QHREDGS treatment on BJ1D iPS cell proliferation.
Figure 17:
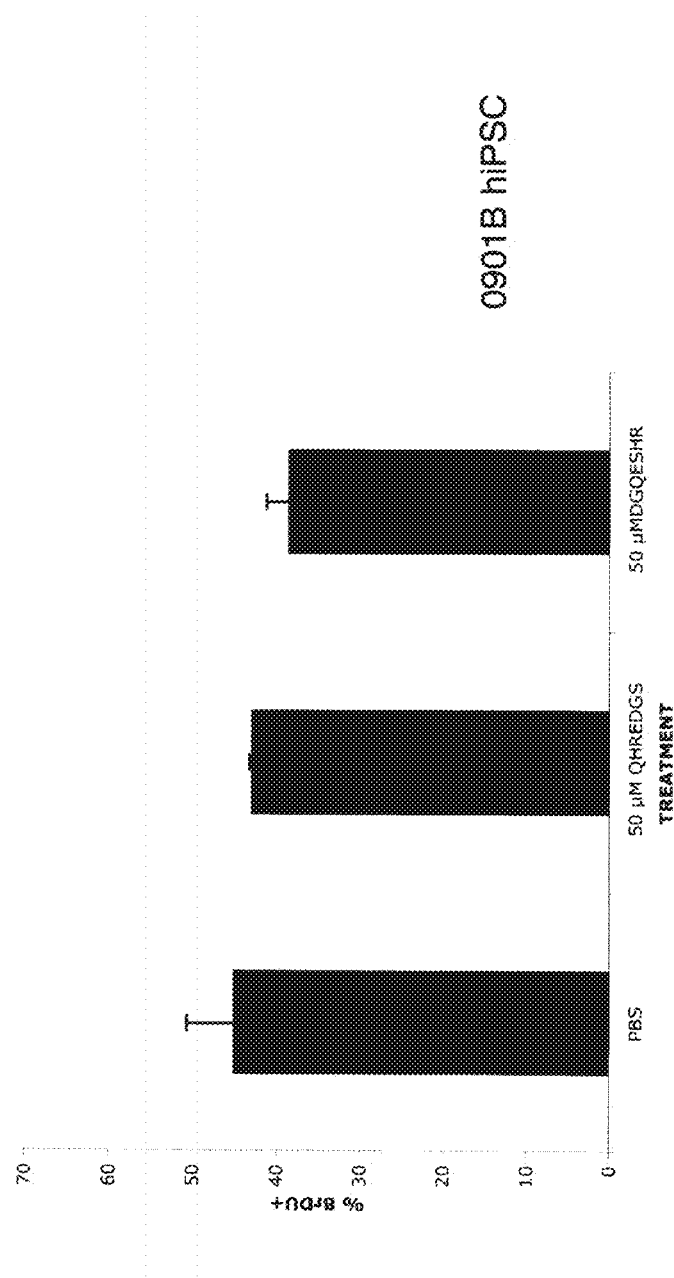
FIG. 17 graphically illustrates the effect of QHREDGS treatment on 0901 iPS cell proliferation.
Figure 18:
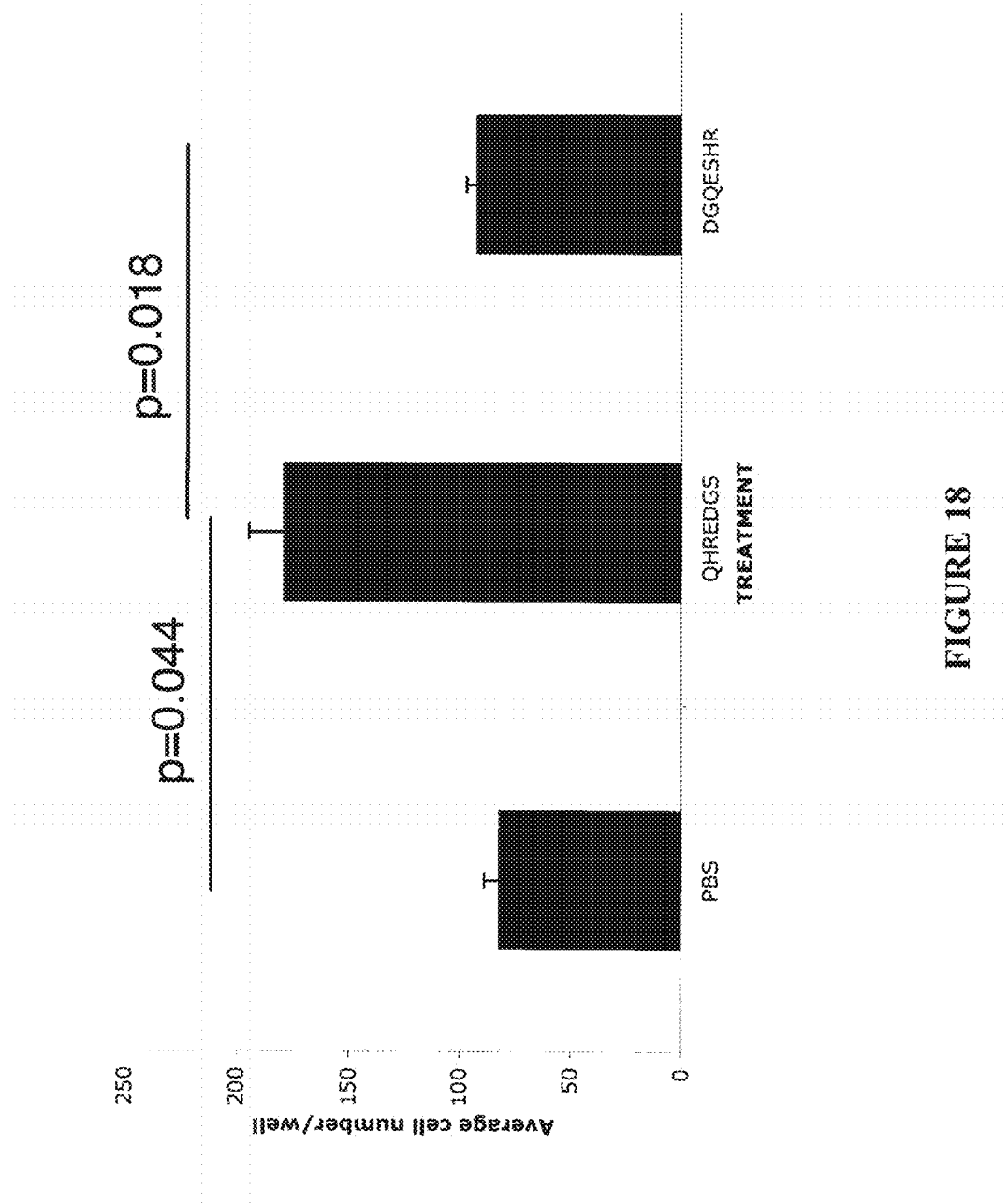
FIG. 18 graphically illustrates the effect of QHREDGS treatment on total cell number of monolayer cultivated human ESC-derived cardiac cells (Hes2)

The effects of QHREDGS on cell growth and proliferation rate were studied to determine whether or not the increase in cell number and colony number in the QHREDGS treated groups could be attributed to cell survival alone, or to an increase in proliferation. It was found that after 5 passages of treatment with the 50 μM QHREDGS peptide, human iPS cells still express Ki67, a marker for proliferative cells, but the rate of proliferation, measured through the incorporation of BrdU during a 1 hr pulse, remained the same in all treatment groups for both BJ1D (FIG. 16) as well as 0901B (FIG. 17). This indicates that QHREDGS positively impacts cloning efficiency (27% increase vs <1% for BJ1 D cells, and 48% increased vs 22% for 0901B cells) as well as cell numbers.

Example 5

Effect on Viability of Human ESC-Derived Cardiac Cells

Methods and Materials

Human ESC-derived cardiac cell culture, were derived from Day 20 EBs, consisting of greater than 50% cardiomyocytes obtained by directed differentiation of human ES (Hes2) cells as described by Yang et al. (*Nature* 453, 524-528 (2008)). EBs were dissociated using Collagenase I (Invitrogen) for 2 hrs and 0.05% Trypsin-EDTA (Invitrogen) for 5 min and plated at 40000 cells/cm$^2$ onto 0.2% gelatin-coated plates in Stempro 34 medium supplemented with VEGF (10 ng/ml) and DKK1 (150 ng/ml). Cells were cultured in the presence of 50 μM QHREDGS, 50 μM DGQESHR (Biomatik) or PBS until they formed a beating monolayer, around 10 days. Peptides were replenished during media changes every 3 days. 100 μM $H_2O_2$ (Sigma, dissolved in PBS) was added to culture media for 10 min, washed, and analyzed immediately for CFDA-Live/PI-Dead. Live cells were counted using the cell counter plug in for ImageJ. 0.5 μM or 2.5 μM taxol (Sigma, dissolved in DMSO) was added to culture media for 24 hrs, and the extent of apoptosis was analyzed immediately using the Apo-ONE Homogeneous Caspase Assay (Promega), or TUNEL assay (Roche) as described above. A PBS control was used for $H_2O_2$ and DMSO control was used for taxol.

Results

Figure 19:
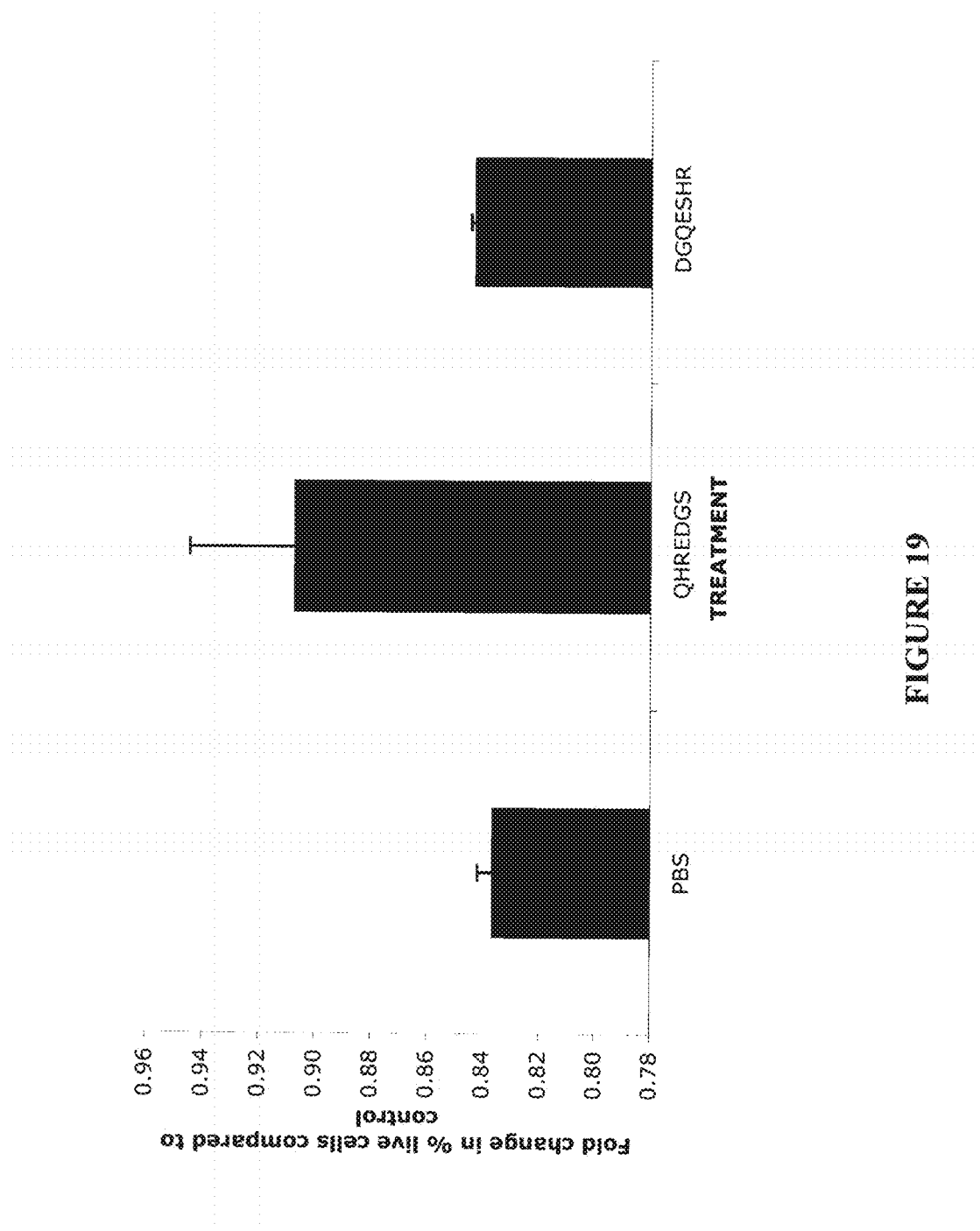
FIG. 19 graphically illustrates the effect of QHREDGS treatment on survival of human ESC-derived cardiac cells (Hes2)
Figure 20:
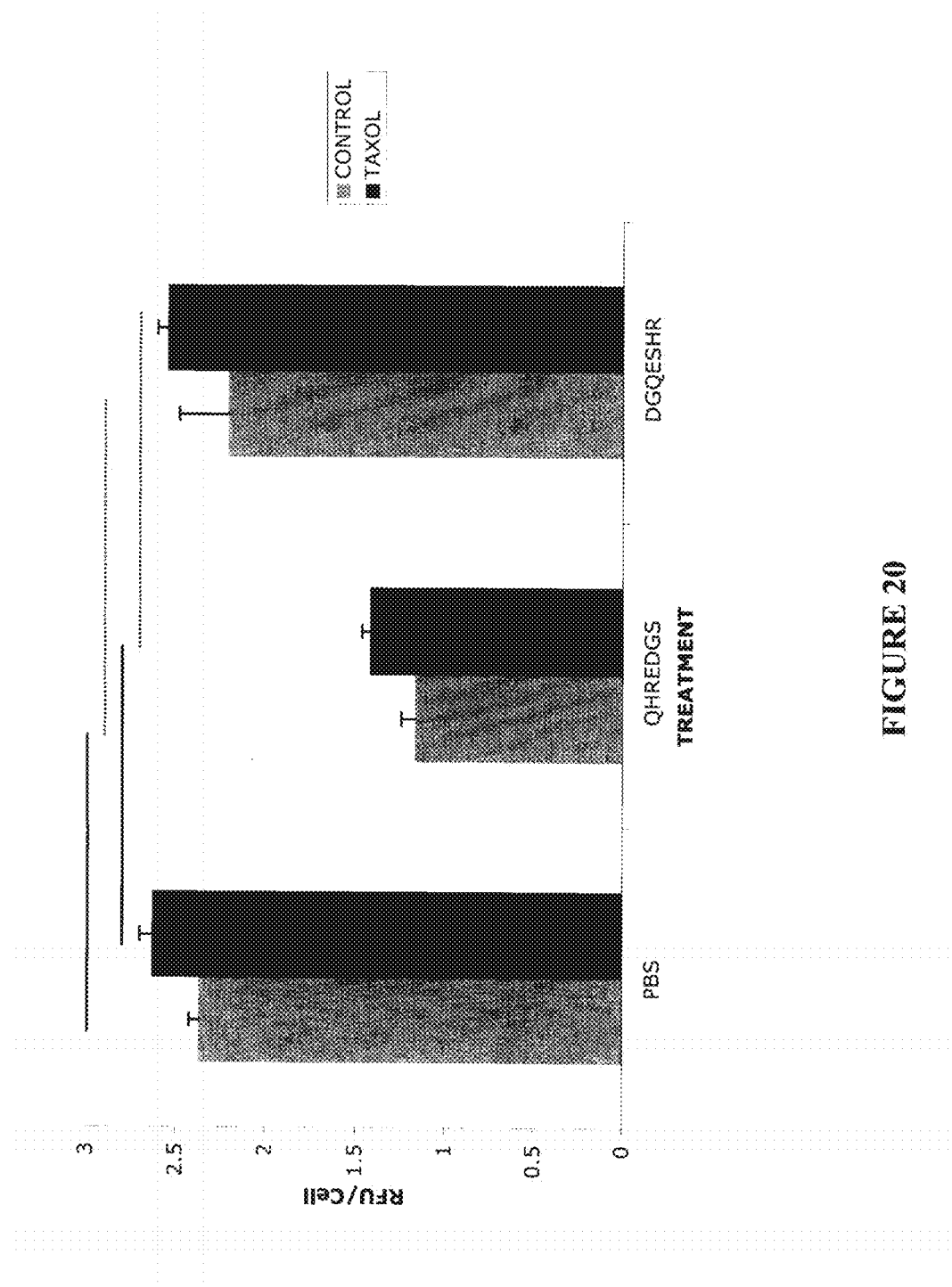
FIG. 20 graphically illustrates the effect of QHREDGS treatment on human ESC-derived cardiac cell apoptosis as determined using the Caspase 3/7 assay before and after overnight taxol treatment.
Figure 21:
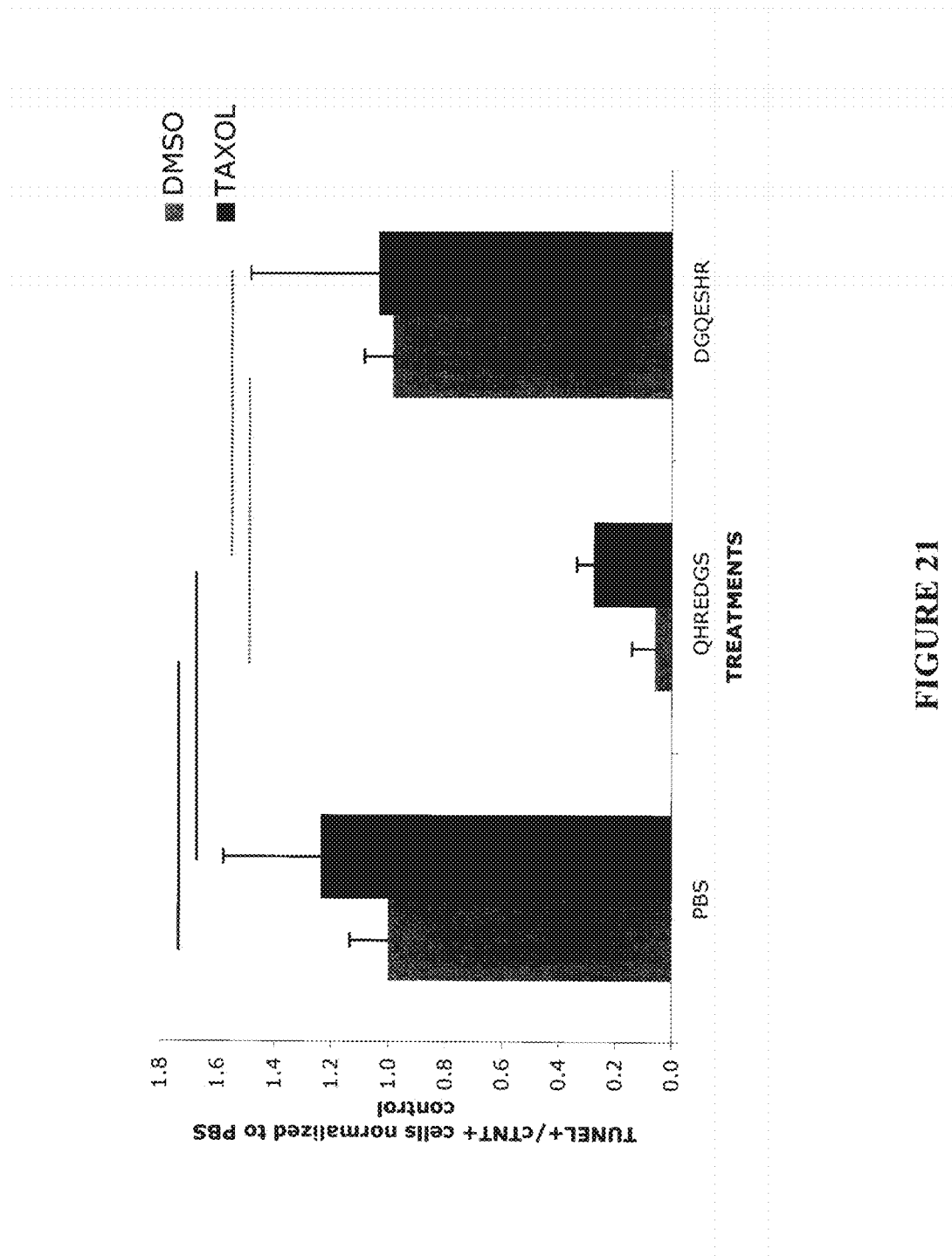
FIG. 21 graphically illustrates the effect of QHREDGS treatment on human ESC-derived cardiac cell apoptosis as determined using the TUNEL assay before and after overnight taxol treatment.

The effect of soluble QHREDGS on the survival of human ESC-derived cardiac cells from day 20 EBs was tested. Cardiac cells, consisting of greater than 50% contracting cardiomyocytes, were obtained through the directed differentiation of human ES cells, as described in Yang et al. *Nature* 453, 524-528 (2008), and plated as a monolayer on 0.2% gelatin in the presence of 50 μM QHREDGS, 50 μM DGQESHR scrambled peptide, or PBS control. Following the formation of a beating monolayer at 10 days of plating, cells were exposed to either $H_2O_2$ for 10 min to increase reactive oxygen species, or taxol for 24 hrs to induce apoptosis. It was found that the number of cardiac cells/well increased in the QHREDGS treated group by greater than 2-fold compared to the PBS control (p=0.044) and the DGQESHR scrambled peptide control (p=0.018). Furthermore, treatment with QHREDGS resulted in enhanced viability of cardiac cells when exposed to 100 μM $H_2O_2$ (FIG. 19) as determined by CFDA/PI assay for % Live-CFDA/Dead-PI. To determine whether apoptosis is reduced in peptide treated groups, an assay to determine levels of Caspase 3/7 activation (FIG. 20) was conducted, as well as the number of TUNEL cells (FIG. 21). Co-localization of TUNEL and cTnT allows us to determine the amount of cardiomyocytes that are affected by apoptosis (FIG. 21). It was found that QHREDGS treatment reduces the basal apoptosis levels in cardiac cells by 2-fold (FIG. 20) as well as cardiomyocytes by greater than 10-fold (FIG. 21). Increased survival of human cardiomyocytes is especially important for successful cell therapies and QHREDGS may be used to prevent apoptosis and allow increased survival of injected cells.

The invention claimed is:

1. A biomaterial conjugate comprising a non-naturally occurring peptide consisting of the amino acid sequence QHREDGS (SEQ ID NO: 2) conjugated to a biomaterial.

2. The biomaterial conjugate as defined in claim 1, comprising a natural or synthetic biomaterial.

3. The biomaterial conjugate as defined in claim 1, wherein the biomaterial is selected from the group consisting of chitosan, alginate, agarose, methylcellulose, hyaluronan, collagen, laminin, matrigel, fibronectin, vitronectin, poly-l-lysine, proteoglycans, fibrin glue, gels made by decellularization of engineered and natural tissues, and a combination thereof.

4. The biomaterial conjugate as defined in claim 1, wherein the biomaterial is selected from the group consisting of polyglycolic acid (PGA), polylactic acid (PLA) and combinations of PGA and PLA such as PLGA, poly ε-caprolactone, polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), self assembling peptide hydrogels, AcN-RARADADARARADADA-CNH, polyurethanes, poly(isopropylacrylamide), poly(N-isopropylacrylamide), [poly(NIPAM)] and combinations thereof.

5. A method of reducing cell apoptosis in cardiac cells, comprising administering to the cells of a biomaterial conjugate as defined in claim 1.

6. The method of claim 5, wherein the biomaterial conjugate is administered in an amount of up to about 500 micromolar.

7. A method of reducing stem cell or progenitor cell apoptosis, comprising administration to the cell of a biomaterial conjugate as defined in claim 1.

8. The method of claim 7, wherein the cell is selected from the group consisting of embryonic stem cells, adipose stem cells, mesenchymal stem cells, induced pluripotent stem cells, hematopoietic stem cells and cardiovascular progenitor cells.

9. A method of treating a condition involving cardiac cell death or apoptosis in a mammal, comprising administering to the mammal a biomaterial conjugate as defined in claim 1.

10. The method of claim 9, wherein the condition is selected from the group consisting of myocardial infarction, congestive heart failure, ischemia reperfusion injury, cardiac ischemia-reperfusion injury, myocardial infarction, cardiac catheterization, circulatory arrest on cardiopulmonary bypass, heart transplant and resuscitation from cardiac arrest.

* * * * *